US008846903B2

(12) United States Patent
Bialer et al.

(10) Patent No.: US 8,846,903 B2
(45) Date of Patent: Sep. 30, 2014

(54) ACYL-UREA DERIVATIVES AND USES THEREOF

(75) Inventors: Meir Bialer, Jerusalem (IL); Boris Yagen, Jerusalem (IL); Jakob Avi Shimshoni, Rechovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1078 days.

(21) Appl. No.: 12/666,703

(22) PCT Filed: Jun. 25, 2008

(86) PCT No.: PCT/IL2008/000870
§ 371 (c)(1),
(2), (4) Date: Jul. 7, 2010

(87) PCT Pub. No.: WO2009/001356
PCT Pub. Date: Dec. 31, 2008

(65) Prior Publication Data
US 2010/0280124 A1   Nov. 4, 2010

Related U.S. Application Data

(60) Provisional application No. 60/929,387, filed on Jun. 25, 2007, provisional application No. 61/006,317, filed on Jan. 7, 2008.

(51) Int. Cl.
*C07D 201/16* (2006.01)
*C07C 275/50* (2006.01)

(52) U.S. Cl.
CPC .................................... *C07C 275/50* (2013.01)
USPC .................................. 540/1; 514/594; 546/44

(58) Field of Classification Search
None
See application file for complete search history.

(56) References Cited

U.S. PATENT DOCUMENTS 2,135,064 A  *  11/1938  Whitmore et al. .............. 564/45

FOREIGN PATENT DOCUMENTS

JP         11079983 A   *   3/1999
WO    WO 2009/001356       12/2008

OTHER PUBLICATIONS

Kuisma et al, Epilepsia 36(12);1241-1243, 1995.*
Cannon et al, J. Neurosurg. 95:1053-1056, 2001.*
Hauser, G.H. Sergievsky Center, College of Physicians and Surgeons, Columbia University, New York, NY. Neurology [1990, 40(5 Suppl. 2):9-13].*
International Preliminary Report on Patentability Dated Jan. 14, 2010 From the International Bureau of WIPO Re.: Application No. PCT/IL2008/000870.
International Search Report Dated Jan. 7, 2009 From the International Searching Authority Re.: Application No. PCT/IL2008/000870.
Written Opinion Dated Jan. 7, 2009 From the International Searching Authority Re.: Application No. PCT/IL2008/000870.
Shimshoni et al. "Potent Anticonvulsant Urea Derivatives of Constitutional Isomers of Valproic Acid", Journal of Medicinal Chemistry, XP002505000, 50(25): 6419-6427, 2007.
Spielman et al. "Anticonvulsant Drugs. II. Some Acylureas", Journal of the American Chemical Society, XP000940775, 70: 4189-4191, Dec. 1, 1948.
Volwiler et al. "Some Alkyl and Aryl Amides and Ureides as Hypnotics", Journal of the American Chemical Society, XP002504998, 58(8): 1352-1354, 1936.
Office Action Dated Aug. 23, 2012 From the Israel Patent Office Re. Application No. 202966 and Its Translation Into English.

* cited by examiner

*Primary Examiner* — Wu-Cheng Winston Shen
*Assistant Examiner* — Jean Cornet

(57) ABSTRACT

Novel acyl-urea containing compounds, processes of preparing same, compositions containing same and uses thereof in the treatment of neurological diseases and disorders such as epilepsy, neuropathic pain, bipolar disorder, status epilepticus, chemically-induced convulsions and/or seizure disorders, febrile convulsions conditions, metabolic disturbances and a sustenance withdrawal conditions, are provided. Also provided are uses of these and other acyl-urea containing compounds in the treatment of neurological diseases and disorders.

2 Claims, No Drawings

US 8,846,903 B2

ACYL-UREA DERIVATIVES AND USES THEREOF

RELATED APPLICATIONS

This Application is a National Phase of PCT Patent Application No. PCT/IL2008/000870 having International filing date of Jun. 25, 2008, which claims the benefit of U.S. Provisional Patent Application Nos. 61/006,317 filed on Jan. 7, 2008, and 60/929,387 filed on Jun. 25, 2007. The contents of the above Applications are all incorporated herein by reference.

FIELD AND BACKGROUND OF THE INVENTION

The present invention, in some embodiments thereof, relates to novel acyl-urea containing compounds, and to uses of acyl-urea containing compounds in a variety of therapeutic applications, including, for example, neurological diseases and disorders such as epilepsy, neuropathic pain and bipolar disorders.

Epilepsy, also referred to in the art as a seizure disorder, is a chronic disorder of the central nervous system (CNS), characterized either by recurrent and unprovoked episodic loss of attention or sleepiness or by severe convulsions with loss of consciousness called seizures or fits. The seizures are considered as transient symptoms which are attributed to irregular immoderate or coincident neuronal activity in the brain. This incurable yet typically therapeutically controlled medical condition affects about 0.5% of the population, whereas about 1.5-5.0% of the population may have a seizure in their lifetime at any age.

Prolonged seizures may lead to the development of Status epilepticus (SE), which is a life threatening cerebral state of a persistent seizure. SE can be defined broadly as one continuous seizure or a series of recurrent seizures wherein the subject does not regain consciousness between seizures for longer than 30 minutes. It is believed that 5 minutes are sufficient to cause irreparable damage to the neurons, and in SE cases seizures are unlikely to terminate spontaneously by that time. In a subject known to suffer from epilepsy, SE can be brought about or be aggravated by poor compliance to treatment (adherence to medication regimen), alcohol withdrawal and/or metabolic disturbances. As a primary presentation it may indicate a brain tumor or abscess. SE was also reported to be caused by various nerve agents (organophosphates) such as sarin, VX and soman.

Current treatment of epilepsy typically consists of oral administration of anticonvulsants or antiepileptic drugs (AEDs). This symptomatic treatment is aimed at reducing the number and severity of future seizures. The efficacy of AEDs depends on the patient's response to a particular AED, which in turn is selected according to the type and severity of the seizure. Some epileptic patients are known to respond well to one AED and may respond poorly or even worsen the condition by others. When the epileptic condition seems not to respond to the use of AEDs, it is referred to as "refractory epilepsy", which is typically treated by brain surgery to remove the abnormal brain cells that are causing the seizures, or by a vagal nerve stimulator, which is implanted in the chest, which helps reducing the number of seizures.

Four major antiepileptic drugs (AEDs) are currently used for the treatment of epilepsy (epileptic seizures and convulsions), which include phenyloin (marketed as Dilantin® in the USA and as Epanutin® in the UK), carbamazepine (sold under the brand-names Biston, Calepsin, Carbatrol, Epitol, Equetro, Finlepsin, Sirtal, Stazepine, Tegretol, Telesmin, Timonil), phenobarbital (also known as phenobarbitone or Luminal®) and valproic acid (VPA). However, about 25% of the patients do not respond to the current medications. Furthermore, AEDs are administered repetitively as chronic treatment and the adverse effects associated with antiepileptic therapy are of a major concern. The major established AEDs are associated with some rare but severe side effect such as teratogenicity and other adverse effects that limit their use.

Status epilepticus is typically treated with benzodiazepines such as diazepam, clonazepam, lorazepam phenobarbital, phenyloin and lorazepam. Phenyloin and it's prodrug fosphenyloin as well as other hydantoin derivatives are also used to treat SE, and are typically co-administered with a benzodiazepine phenobarbital or barbiturate. Barbiturates such as phenobarbital, secobarbital, thiopental or pentobarbital, are still used today to treat SE if benzodiazepines or the hydantoins are not an option, primarily by induction of a barbituric coma. In that respect of coma-causing agents, general anesthetics such as propofol and lidocaine are used where barbiturates are ineffective or cannot be used for some other reason.

Valproic acid is a broad-spectrum antiepileptic and CNS active agent, which is still in use as an anticonvulsant and mood-stabilizing drug in the treatment of epilepsy and bipolar disorder. It has also been used in the treatment of neuropathic pain, myoclonus, schizophrenia and for migraine prophylaxis. VPA is believed to act through a combination of mechanisms, namely as a membrane stabilizer; as a GABA transaminase inhibitor, thereby enhancing GABA signaling; and as a serotonergic inhibitor which reduces NMDA-receptor mediated glutamate excitation. In principle, such multilevel action is highly advantageous, promising improved efficacy with reduced side effects. However, the clinical use of VPA is limited by two rare, but potentially life-threatening side effects, teratogenicity and hepatotoxicity that restrict its utilization in women of child bearing age and in children. While VPA's teratogenicity is associated with the parent compound [1], its hepatotoxicity results from biotransformation into hepatotoxic metabolites with a terminal double bond, specifically 4-ene-VPA [2-4].

Extensive efforts have therefore been directed towards therapeutically active derivatives of VPA which exhibit improved activity and/or reduced side effects.

Therapeutically active derivatives of VPA include the salt sodium valproate which is used in anticonvulsant formulations, and valproate semisodium, which is used as an anticonvulsant and a mood stabilizer. A homologue of VPA wherein one of the alkyl chains is three carbons longer, arundic acid ((R)-(−)-2-propyloctanoic acid, also known as ONO-2506), is currently under clinical development for the potential treatment of stroke, as well as of other neurodegenerative diseases including amytrophic lateral sclerosis (ALS), Alzheimer's disease and Parkinson's disease [5].

A series of VPA-amide analogue and derivatives thereof was developed via a series of structure (pharmacokinetic/pharmacodynamic) activity relationship studies, and were found to exhibit improved anticonvulsant activity while avoiding teratogenicity and hepatotoxicity [6-9]. Some of these VPA amide derivatives were also active in animal models of neuropathic pain [10, 11] and bipolar disorder [12, 13].

Urea is an integral part of the heterocyclic chemical structures of three leading AEDs, namely phenobarbital, phenyloin and carbamazepine. These drugs consist of a lipophilic moiety delineated by phenyl-alkyl in phenobarbital, diphenyl in phenyloin and dibenzazepine in carbamazepine, and a hydrophilic moiety, containing a ring fused urea molecule.

The presence of urea in all of these drugs implies that it plays an important role in the anticonvulsant pharmacophore [6, 14].

Acyl-urea containing compounds are known for many decades [15-18]. These compounds have been considered promising anticonvulsants [19] and as sedative or hypnotic agents [20]. Spielman and coworkers [19] synthesized a series of acyl-urea derivatives using a variety of branched aliphatic and aromatic residues, and evaluated as potential anticonvulsant agents using maximal electroshock seizure test (MES) and subcutaneous metrazol test (scMet) in mice. In this series, Spielman reports that several derivatives of acyl-urea demonstrated potent anticonvulsant activity, including 2-ethyl-3-methylvalerylurea, 2-ethylcaproylurea and 2-isopropyl-$\Delta^4$-pentenoylurea, whereby other derivatives were found non-active. The anticonvulsant profile of valproylurea was also evaluated by Tantisira et al. [21] on mice MES and scMET models, who showed an excellent protection in both models with a favorable protective index compared to valproic acid.

Other acyl-urea containing compounds have been previously reported and studied as drugs for the treatment of psychiatric and neurological conditions. An example is the drug Sedormid (allyl-isopropyl-acetyl urea) which was used as a mild anxiolytic and sedative agent until it was found toxic and therefore is no longer marketed.

U.S. Pat. No. 3,282,998 teaches the synthesis of (2-ethyl-3-methyl-pentanoyl)-urea, and Goldstein et al. [22] reported studies relating to this compound, known as the drug Capuride (Pacinox®) which was indicated for sleep disorders, as a minor tranquilizer and anti-anxiety agent. None of these publications relates to the stereochemistry of the compound.

One of the observations which stem from these seminal studies is the effect of seemingly minor structural changes in the acyl group, such as the location, addition or elimination of even a single methyl group or more, on the activity of the resulting compound.

A new and highly effective AED, 2,2,3,3-tetramethylcyclopropylcarbonylurea, has recently been synthesized and tested [6]. This acyl-urea derivative of cyclopropane showed anticonvulsant activity in both the scMet and the MES model tests in mice and rats [23], with a protective index, e.g. median neurological toxic dose to median effective dose ratio ($TD_{50}$-to-$ED_{50}$ ratio) of 18.5 in the MES test, compared to 1.6 which was measured and calculated for valproic acid.

U.S. Pat. No. 6,417,399 by two of the present inventors relates to the individual stereoisomers of the drug valnoctamide (a mixture of four stereoisomer kinds of 2-ethyl-3-methyl-pentanamide, VCD) which are shown to be more potent than any mixture thereof in the treatment of neurological and psychotic disorders such as epilepsy, pain and affective disorders, and useful as tranquilizers. This disclosure further teaches a method for stereoselective separation and quantification of each of the four stereoisomers from a racemic mixture of VCD or from plasma of patients treated with the racemic drug, and to a unique method for the synthesis of the individual stereoisomers.

SUMMARY OF THE INVENTION

The present inventors have now prepared and successfully practiced various acyl-urea containing compounds as agents for the treatment of neurological diseases and disorders.

Thus, according to one aspect of the present invention there is provided a compound having the general Formula I:

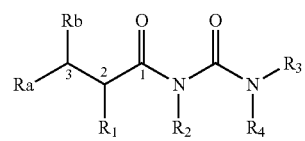

Formula I wherein:
$R_1$-$R_4$ are each independently hydrogen or an alkyl having from 1 to 10 carbon atoms; and
Ra and Rb are each methyl,
with the proviso that when each of $R_2$-$R_4$ is hydrogen, $R_1$ is an alkyl having from 3 to 10 carbon atoms.

According to further features in some embodiments of the invention described below, each of $R_2$-$R_4$ is hydrogen.

According to still further features in the described embodiments $R_1$ is propyl.

According to further features in some embodiments of the invention described below, each of $R_2$-$R_4$ is hydrogen, and $R_1$ is propyl.

According to further features in some embodiments of the invention described below, each of $R_2$-$R_4$ is hydrogen, $R_1$ is propyl, and the stereo-configuration at position 2 is selected from the group consisting of an R-configuration, an S-configuration and a mixture thereof.

According to further features in some embodiments of the invention described below, each of $R_2$-$R_4$ is hydrogen, and $R_1$ is isopropyl.

According to another aspect of the present invention there is provided a pharmaceutical composition which includes, as an active ingredient, the compound defined by Formula I, and a pharmaceutically acceptable carrier.

According to further features in some embodiments of the invention described below, the pharmaceutical composition is being packaged in a packaging material and identified in print, in or on the packaging material, for use in the treatment of a neurological disease or disorder.

According to still another aspect of the present invention there is provided a pharmaceutical composition, being packaged in a packaging material and identified in print, in or on the packaging material, for use in the treatment of a neurological disease or disorder, the composition comprising a compound having a general formula selected from the group consisting of Formula II and III:

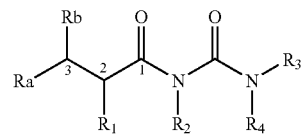

Formula II

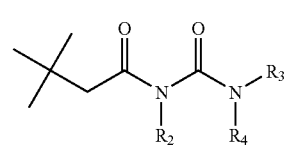

Formula III wherein:
$R_1$-$R_4$, Ra and Rb are each independently hydrogen or an alkyl having from 1 to 10 carbon atoms.

According to yet another aspect of the present invention there is provided a method of treating a medical condition associated with a neurological disorder, the method is effected by administering to a subject in need thereof a therapeutically effective amount of a compound having a general formula selected from the group consisting of Formula II and III as defined herein.

According to further features in some embodiments of the invention described below, the therapeutically effective amount ranges from about 0.1 mg/kg body to about 100 mg/kg body. Alternatively, the therapeutically effective amount ranges from about 5 mg/kg body to about 70 mg/kg body, and in other embodiments the therapeutically effective amount ranges from about 10 mg/kg body to about 40 mg/kg body.

According to an additional aspect of the present invention there is provided a use of a compound having a general formula selected from the group consisting of Formula II and III as defined herein, in the manufacture of a medicament for the treatment of a neurological disease or disorder.

According to further features in some embodiments of the invention described below, the compound has the general Formula II.

According to still further features in the described embodiments, each of $R_2$-$R_4$ is hydrogen in the compound having the general Formula II.

According to still further features in the described embodiments, each of $R_2$-$R_4$ is hydrogen and $R_1$ is propyl in the compound having the general Formula II.

According to still further features in the described embodiments, each of $R_2$-$R_4$ is hydrogen, $R_1$ is propyl, and the stereo-configuration at position 2 is selected from the group consisting of an R-configuration, an S-configuration and a mixture thereof in the compound having the general Formula II.

According to still further features in the described embodiments, each of $R_2$-$R_4$ is hydrogen and $R_1$ is isopropyl in the compound having the general Formula II.

According to still further features in the described embodiments, each of $R_2$-$R_4$ is hydrogen and Rb is methyl in the compound having the general Formula II.

According to still further features in the described embodiments, each of $R_2$-$R_4$ and Rb is hydrogen in the compound having the general Formula II.

According to still further features in the described embodiments, each of $R_2$-$R_4$ and Rb is hydrogen, Ra is propyl and $R_1$ is ethyl in the compound having the general Formula II.

According to still further features in the described embodiments, each of $R_2$-$R_4$ and Rb is hydrogen, Ra is ethyl and $R_1$ is propyl in the compound having the general Formula II.

According to still further features in the described embodiments, each of $R_1$-$R_4$ is hydrogen, and Ra and Rb is methyl in the compound having the general Formula II.

According to still further features in the described embodiments, each of $R_2$-$R_4$ and Ra is hydrogen, and each of Rb and $R_1$ is methyl in the compound having the general Formula II.

According to still further features in the described embodiments, the compound of the composition, method or use presented above is having the general Formula III, and each of $R_2$-$R_4$ is independently hydrogen.

According to still further features in the described embodiments, the compounds of the composition, method or use presented above are selected from the group consisting of:

1-(2-isopropylpentanoyl)urea (Compound 1, PIU), having the formula:

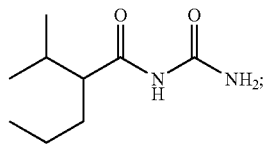

R-1-(2-isopropylpentanoyl)urea (Compound 1R, R-PIU), having the formula:

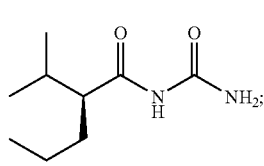

S-1-(2-isopropylpentanoyl)urea (Compound 1S, S-PIU), having the formula:

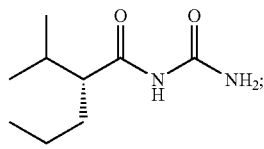

1-(2-isopropyl-3-methylbutanoyl)urea (Compound 2, DIU), having the formula:

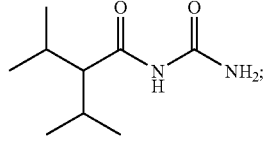

1-(3,3-dimethyl-butyryl)urea (Compound 3, TBU), having the formula:

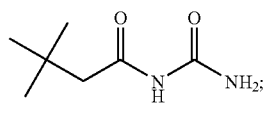

1-(2-ethyl-hexanoyl)-urea (Compound 5, EBU), having the formula:

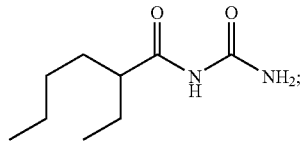

1-(2-propyl-pentanoyl)-ureaorvalproate urea (Compound 6, VPU), having the formula:

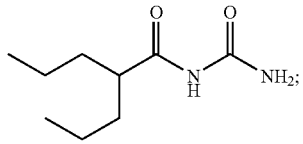

2-methylbutanoylurea (Compound 8), having the formula:

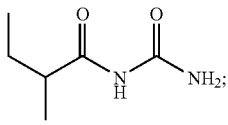

and 2,2-dimethylpropanoylurea_or 1-(pivaloyl)urea (Compound 9), having the formula:

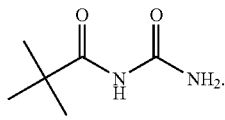

According to further features in some embodiments of the invention described below, the neurological disorder treatable using compound having general Formulae II and III, is selected from the group consisting of epilepsy, convulsions, seizure disorder, complex partial seizures, status epilepticus, a chemically-induced convulsion and/or seizure disorder, a febrile convulsion condition, a metabolic disturbance and a substance withdrawal condition, spasticity, skeletal muscle spasms, restless leg syndrome, anxiety, stress, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and a bipolar disorder, with the proviso that when each of $R_2$-$R_4$ is hydrogen, Ra is methyl or ethyl and Rb is methyl, $R_1$ is an alkyl having from 3 to 10 carbon atoms.

According to some embodiments of the present invention the neurological disorder treatable using compounds having general Formulae II and III, is selected from the group consisting of status epilepticus, a chemically-induced convulsion and/or seizure disorder, a febrile convulsion condition, a metabolic disturbance and a substance withdrawal condition.

According to an additional aspect of the present invention there is provided a process of preparing the novel compounds described herein, the process comprising:
reacting a compound having the general Formula IV:

Formula IV

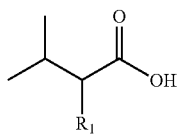

wherein $R_1$ is hydrogen or an alkyl having from 1 to 10 carbon atoms,
with a compound having the general Formula V:

Formula V

wherein $R_2$-$R_4$ are each independently hydrogen or an alkyl having from 1 to 10 carbon atoms,
with the proviso that when each of $R_2$-$R_4$ is hydrogen, $R_1$ is an alkyl having from 3 to 10 carbon atoms.

According to further features in some embodiments of the invention described below, prior to reacting, the compound having the general Formula IV is converted into a reactive carboxylic derivative thereof. Alternatively the reactive carboxylic derivative is an acyl-halide.

According to further features in some embodiments of the invention described below, the compound having general Formula IV is obtained by reacting isovaleric acid with an alkylating agent having the general Formula VI:

$$R_1-X \qquad \text{Formula VI.}$$

According to another aspect of the present invention there is provided a pure (isolated) stereoisomer of (2-ethyl-3-methyl-pentanoyl)-urea.

According to further features in some embodiments of the invention described below, the stereoisomer of (2-ethyl-3-methyl-pentanoyl)-urea is selected from the group consisting of ((2S)-2-ethyl-(3S)-3-methyl-pentanoyl)-urea, ((2S)-2-ethyl-(3R)-3-methyl-pentanoyl)-urea, ((2R)-2-ethyl-(3S)-3-methyl-pentanoyl)-urea and ((2R)-2-ethyl-(3R)-3-methyl-pentanoyl)-urea.

According to another aspect of the present invention there is provided a pharmaceutical composition packaged in a packaging material and identified in print, in or on the packaging material, for use in the treatment of a neurological disease or disorder, the composition comprising at least one of pure (isolated) stereoisomer of (2-ethyl-3-methyl-pentanoyl)-urea, as described herein.

According to yet another aspect of the present invention there is provided a method of treating a medical condition associated with a neurological disorder, the method comprising administering to a subject in need thereof a therapeutically effective amount of at least one pure stereoisomer of (2-ethyl-3-methyl-pentanoyl)-urea.

According to yet another aspect of the present invention there is provided a use of at least one pure stereoisomer of (2-ethyl-3-methyl-pentanoyl)-urea, in the manufacture of a medicament for the treatment of a neurological disease or disorder.

According to further features in some embodiments of the invention described below, the neurological disorder is selected from the group consisting of epilepsy, convulsions, seizure disorder, complex partial seizures, status epilepticus, a chemically-induced convulsion and/or seizure disorder, a febrile convulsion condition, a metabolic disturbance and a substance withdrawal condition, spasticity, skeletal muscle spasms, restless leg syndrome, anxiety, stress, sleep disorder, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and a bipolar disorder. Alternatively the neurological disorder is selected from the group consisting of epilepsy, status epilepticus, a chemically-induced convulsion and/or seizure disorder, a febrile convulsion condition, a metabolic disturbance and a substance withdrawal condition, complex partial seizures, neuropathic pain and bipolar disorder.

According to another aspect of the present invention there is provided a pharmaceutical composition packaged in a packaging material and identified in print, in or on the packaging material, for use in the treatment of a neurological disease or disorder selected from the group consisting of epilepsy, convulsions, seizure disorder, complex partial seizures, status epilepticus, a chemically-induced convulsion and/or seizure disorder, a febrile convulsion condition, a metabolic disturbance and a substance withdrawal condition, spasticity, skeletal muscle spasms, restless leg syndrome, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and a bipolar disorder, the composition comprising a compound having a general formula selected from the group consisting of Formula II and III:

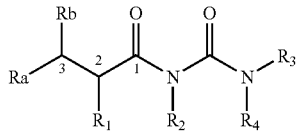

Formula II

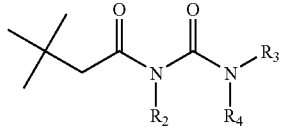

Formula III an enantiomer, a diastereomer, a prodrug, a hydrate, a solvate or a pharmaceutically acceptable salt thereof,
wherein:
$R_1$-$R_4$, Ra and Rb are each independently hydrogen or an alkyl having from 1 to 10 carbon atoms;
with the provisos that:
when each of $R_2$-$R_4$ is hydrogen and each of Ra and Rb is methyl, $R_1$ is an alkyl having from 3 to 10 carbon atoms; and
when each of $R_2$-$R_4$ is hydrogen, Ra is ethyl and Rb is methyl, $R_1$ is an alkyl having from 2 to 10 carbon atoms.

According to yet another aspect of the present invention there is provided a method of treating a neurological disease or disorder selected from the group consisting of epilepsy, convulsions, seizure disorder, complex partial seizures, status epilepticus, a chemically-induced convulsion and/or seizure disorder, a febrile convulsion condition, a metabolic disturbance and a substance withdrawal condition, spasticity, skeletal muscle spasms, restless leg syndrome, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and a bipolar disorder, the method comprising administering to a subject in need thereof a therapeutically effective amount of a compound having a general formula selected from the group consisting of Formula II and III:

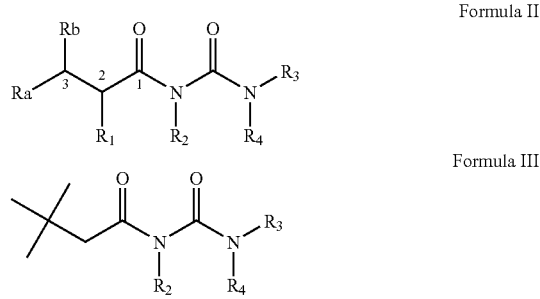

an enantiomer, a diastereomer, a prodrug, a hydrate, a solvate or a pharmaceutically acceptable salt thereof,
wherein:
$R_1$-$R_4$, Ra and Rb are each independently hydrogen or an alkyl having from 1 to 10 carbon atoms;
with the provisos that:
when each of $R_2$-$R_4$ is hydrogen and each of Ra and Rb is methyl, $R_1$ is an alkyl having from 3 to 10 carbon atoms; and
when each of $R_2$-$R_4$ is hydrogen, Ra is ethyl and Rb is methyl, $R_1$ is an alkyl having from 2 to 10 carbon atoms.

According to still another aspect of the present invention there is provided a use of a compound having a general formula selected from the group consisting of Formula II and III:

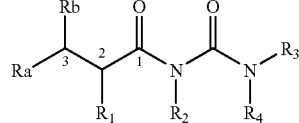

Formula II

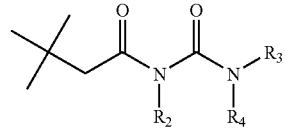

Formula III an enantiomer, a diastereomer, a prodrug, a hydrate, a solvate or a pharmaceutically acceptable salt thereof,
wherein:
$R_1$-$R_4$, Ra and Rb are each independently hydrogen or an alkyl having from 1 to 10 carbon atoms;
with the provisos that:
when each of $R_2$-$R_4$ is hydrogen and each of Ra and Rb is methyl, $R_1$ is an alkyl having from 3 to 10 carbon atoms; and
when each of $R_2$-$R_4$ is hydrogen, Ra is ethyl and Rb is methyl, $R_1$ is an alkyl having from 2 to 10 carbon atoms,
in the manufacture of a medicament for the treatment of a neurological disease or disorder selected from the group consisting of epilepsy, convulsions, seizure disorder, complex partial seizures, status epilepticus, chemically-induced convulsions and/or seizure disorders, febrile convulsion conditions, metabolic disturbances, substance withdrawal conditions, spasticity, skeletal muscle spasms, restless leg syndrome, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and a bipolar disorder.

According to exemplary embodiments, the neurological disease or disorder is epilepsy, status epilepticus, a chemically-induced convulsion and/or seizure disorder, a febrile convulsion condition, a metabolic disturbance, a substance withdrawal condition, neuropathic pain or a bipolar disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

DESCRIPTION OF SPECIFIC EMBODIMENTS OF THE INVENTION

The present invention, in some embodiments thereof, is of novel acyl-urea containing compounds, and of processes of preparing same. The present invention, in some embodiments thereof, is further of uses of acyl-urea containing compounds in the treatment of neurological diseases and disorders such as epilepsy, status epilepticus, chemically-induced convulsions and seizures and other non-epileptic convulsions, neuropathic pain and bipolar disorders.

The acyl-urea containing compounds described herein are characterized by improved efficacy and reduced side effects and hence present a novel family of potent agents for treating a variety of medical conditions.

The acyl-urea containing compounds described herein possess unique and novel therapeutic features that render these compounds superior to other acyl-urea containing compounds known in the art in the treatment of neurological diseases and disorders such as epilepsy.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, acyl-urea containing compounds are well known in the art, and some where considered as promising therapeutic agents in the treatment of epilepsy and other neurological diseases and disorders. For many decades researchers have manipulated valproic acid and acyl-urea containing compounds in an attempt to strike a new path to a more potent antiepileptic drug (AED) and thus created a vast repository of these compounds.

While conceiving the present invention, the present inventors hypothesized that combining some basic structural features of valproic acid with urea may produce effective AEDs. While reducing the present invention to practice it was found that the acyl-urea containing compounds are much more potent as anticonvulsants and possess a higher protective index, than their corresponding acids, and more particularly it was found that urea derivatives of valproic acid are very promising anticonvulsants, possessing the potential in the treatment of several neurological diseases and disorders.

As mentioned hereinabove, one of the observations which stemmed from early studies such as that of Spielman et al. was the effect of seemingly minor structural changes in the acyl group, such as the location, addition or elimination of even a single methyl group or more, on the pharmacologic profile of the resulting compound.

As demonstrated in the Examples section that follows, while reducing the present invention to practice, several acyl-urea containing compounds were prepared and successfully tested for their anticonvulsant activity in animal models. As mentioned hereinabove, it was indeed shown that by selecting the location, addition or elimination of even a single methyl group or more, improved activity is obtained. It was further shown that several acyl-urea containing compounds that were previously prepared and previously tested for anticonvulsant activity in the art, have now been found to exhibit completely different activity levels as compared to the activities reported in the art.

Thus, according to one aspect of the present invention, there is provided a compound having the general Formula I:

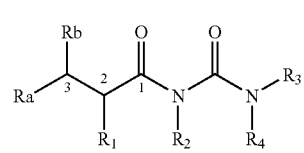

Formula I wherein $R_1$-$R_4$ are each independently hydrogen or an alkyl having from 1 to 10 carbon atoms; and Ra and Rb are each independently methyl.

with the proviso that when each of $R_2$-$R_4$ is hydrogen, $R_1$ is an alkyl having from 3 to 10 carbon atoms.

As used herein, the term "alkyl" describes an aliphatic hydrocarbon including straight chain and branched chain groups. Preferably, the alkyl group has 1 to 10 carbon atoms, and more preferably 1 to 4 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted.

The term "alkyl", as used herein, also encompasses saturated or unsaturated hydrocarbon, hence this term further encompasses alkenyl and alkynyl, however, the term "alkyl" does not encompass allyl (—$CH_2$—CH=$CH_2$).

The term "alkenyl" describes an unsaturated alkyl, as defined herein, having at least two carbon atoms and at least one carbon-carbon double bond. The alkenyl may be substituted or unsubstituted by one or more substituents, as described herein.

The term "alkynyl", as defined herein, is an unsaturated alkyl having at least two carbon atoms and at least one carbon-carbon triple bond. The alkynyl may be substituted or unsubstituted by one or more substituents, as described herein.

The term "urea" as used herein, refers to a —NR'C(=O)—NR''R''', where R', R'' and R''' are each selected from the group consisting of hydrogen, alkyl, cycloalkyl, heteroalicyclic, aryl or heteroaryl, as these terms are defined herein.

The term "acyl", as used herein, refers to an R'—(C=O)—, where R' is as defined herein.

Therefore, the phrase "acyl-urea containing", as used herein, refers to a compound which includes an R'—(C=O)—NR''C(=O)—NR'''R'''' group, where R', R'' and R''' are as defined herein, and R'''' is as defined for R'.

According to some embodiments of the present invention, each of $R_2$, $R_3$ and $R_4$ is hydrogen. Alternatively, one or more of $R_2$-$R_4$ is an N-alkyl, which is a low alkyl having 1 to 4 carbon atoms.

According to other embodiments of the present invention, $R_1$ is propyl.

In some embodiments, $R_2$, $R_3$ and $R_4$ are each hydrogen, and $R_1$ is propyl, resulting in the compound 1-(2-isopropylpentanoyl)urea which is referred to hereinbelow as Compound 1, as demonstrated in the Examples section that follows.

The compound 1-(2-isopropylpentanoyl)urea (Compound 1, see Table 1 hereinbelow) has a chiral center at position 2, as denoted in Formula I. Hence, the present embodiments encompass the racemate, Compound 1, as well as both optically active enantiomers thereof, namely, when the stereo-configuration at position 2 is an R-configuration, resulting in 1-((R)-2-isopropylpentanoyl)urea (Compound 1R, see Table 1 hereinbelow), an S-configuration, resulting in 1-((S)-2-isopropyl-pentanoyl)urea (Compound 1S, see Table 1 hereinbelow), and a mixture of any ratio thereof. Alternatively, the racemate of Compound 1 has a 1:1 enantiomeric ratio.

According to other embodiments, $R_2$, $R_3$ and $R_4$ are each hydrogen, and $R_1$ is isopropyl, resulting in the compound 1-(2-isopropyl-3-methylbutanoyl)urea which is referred to hereinbelow as Compound 2, as demonstrated in the Examples section that follows.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The terms "diastereomers" or "diastereoisomers", as used herein, refer to stereoisomers that are not enantiomers with respect to one another. Diastereomers have more than one chiral center, and can have different physical properties and different reactivity. Diastereoisomers are not mirror images of each other but rather have one or more chiral centers inverted between the two stereoisomers. If a molecule exhibits two chiral centers (two asymmetric carbons), there are up to four possible stereo-configurations and hence up to four possible diastereomers. In the context of the present embodiments, diastereomers include compounds having different chirality in at least one of the two chiral centers at positions 2 and 3 of the compound (see, Formula I).

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

According to the present embodiments, compounds according to general Formula I wherein $R_2$-$R_4$ is hydrogen and $R_1$ is an alkyl having less than 3 carbon atoms (e.g., methyl or ethyl), have been previously described and are therefore excluded from the scope of this aspect of the present invention.

As discussed hereinabove, certain acyl-urea compounds, among which is (2-ethyl-3-methyl-pentanoyl)-urea (VCU, Compound 4) have been prepared and studied as anticonvulsants for many decades [19] and some have also been used as drugs for use in human for treating anxiety and sleep disorders [22]. However, VCU was studied and used as a racemic mixture, and none of the previous disclosures refers to pure isolates of any particular stereoisomer thereof. As discussed hereinabove, other derivatives of valproic acid, and particularly diastereomers of 2-ethyl-3-methyl-pentanoic acid amide, disclosed in U.S. Pat. No. 6,417,399, have been shown to exhibit stereoconfiguration-sensitive activity, or in other words, the stereoconfiguration of these compounds have been shown to have significant impact on their activity, such that purified diastereoisomers have superior activity over that of the racemate.

Hence, according to another aspect of the present invention, there is provided a pure (isolated) stereoisomer of (2-ethyl-3-methyl-pentanoyl)-urea.

More specifically, the stereoisomer of (2-ethyl-3-methyl-pentanoyl)-urea include (2S)-2-ethyl-(3S)-3-methyl-pentanoyl)-urea, (2S)-2-ethyl-(3R)-3-methyl-pentanoyl)-urea, (2R)-2-ethyl-(3S)-3-methyl-pentanoyl)-urea and (2R)-2-ethyl-(3R)-3-methyl-pentanoyl)-urea.

As discussed hereinabove, acyl-urea containing compounds have been known and studied for decades, yet few have been considered as drug candidates, particularly for the treatment of neurological diseases or disorders, and none were shown to possess the qualities which are necessary for a compound to be considered as a drug candidate.

As discussed hereinabove, the present inventors have envisioned that particular acyl-urea containing compounds according to some embodiments presented herein would exhibit highly effective therapeutic activity as compared to valproic acid and other acyl-urea containing compounds, and hence these compounds were developed as, for example, potential antiepileptic drugs. While reducing the present invention to practice, as is demonstrated in the Examples section that follows, it was indeed shown that exemplary acyl-urea containing compounds as presented herein are highly effective therapeutic agents. In particular, it is shown in the Examples section that follows, that this family of compounds displays in vivo therapeutic activity levels which are highly sensitive to small and even minute structural changes in their structure, even at the level of the addition, removal and/or displacement of a single carbon atom in the acyl part of the molecule.

As demonstrated in the Examples section that follows the compounds presented herein were designed and selected so as to, and were indeed shown to, possess a pronounced anticonvulsant and anti-bipolar activities, namely the ability to reduce the effect of chemically and electrically induced seizures and bipolar behavior in rats and mice. Such a therapeutic activity renders these compounds suitable for use as therapeutically active agents for the treatment of neurological diseases and disorders, and particularly conditions which involve seizures and other involuntary convulsions and other mental conditions, as defined and discussed hereinbelow.

Based on the therapeutic activity exhibited by these compounds, according to another aspect of the present invention there is provided a use of the acyl-urea containing compounds, represented in the general Formulae II and III:

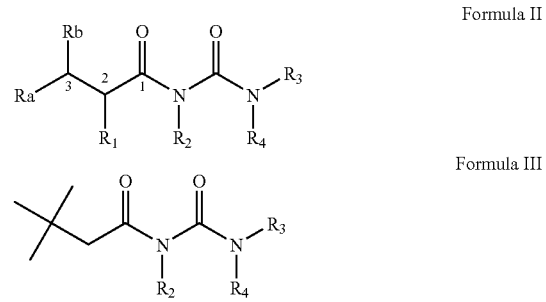

wherein:
$R_1$-$R_4$, Ra and Rb are each independently hydrogen or an alkyl having from 1 to 10 carbon atoms, as well enantiomers, diastereomers, hydrates, solvates or pharmaceutically acceptable salts thereof, as defined hereinabove, in the preparation of a medicament. Alternatively, the medicament is for treating a neurological disease or disorder.

According to the present embodiments, compounds according to general Formula II and III wherein each of $R_2$-$R_4$ is hydrogen, Ra is methyl or ethyl, Rb is methyl and $R_1$ is an alkyl having less than 3 carbon atoms, have been previously described in the context of some particular neurological therapeutic uses, as presented hereinabove, and are therefore excluded from the scope of this aspect of the present invention for those specific indications they were suggested for.

Accordingly, according to another aspect of the present invention, there is provided a method of treating a neurological disease or disorder. The method is effected by administering to a subject in need thereof a therapeutically effective amount of acyl-urea containing compounds as represented in general Formulae II and III above.

As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "neurological disease or disorder" refers to a genetic or acquired dysfunction in one of the component of the brain and spinal cord, namely the central nervous system (CNS), peripheral and cranial nerves (PNS), namely the peripheral nervous system or the autonomic nervous system and the musculoskeletal system. These diseases and disorders express themselves in a variety of behavioral symptoms, motorial symptoms, form disfigurements (deformity, abnormality), neuropathic pain and cognitive disturbances and other physiological symptoms. In the context of the present invention, neurological diseases and disorders include psychiatric diseases and disorders and neurodegenerative diseases and disorders.

According to an exemplary embodiment of the present invention, the neurological disorder comprises seizures, relating to any abnormal electrical discharge in the brain resulting in abnormal synchronization of electrical neuronal activity. Seizures may be due to epilepsy and non epilepsy associated.

For example non epileptic seizures can be caused by chemical agents. As used herein, the phrase "chemically-induced convulsions and/or seizure disorder" refers to a seizure caused by temporary or chronic exposure to an exogenic substance or chemical such as, for example, a toxin (such as, for example, tetanus toxin (tetanospasmin), botulin, tetrodotoxin, batrachotoxin, maurotoxin, agitoxin, charybdotoxin, margatoxin, slotoxin, scyllatoxin, hefutoxin, calciseptine, taicatoxin and calcicludine), an alkaloid (such as ephedrine alkaloids, phenethylamines, amphetamines, tryptamines, mescaline, psilocybin and pilocarpine), a nerve agent, an and an organophosphate (such as, for example, tabun (GA), sarin (GB), soman (GD), cyclosarin (GF), GV, VE, VG, VM, VX, Novichok agents, pulmonary agents, chloropicrin (PS), phosgene (CG) and diphosgene (DP)) and a drug (such as, for example, aminophylline or local anaesthetics as well as antidepressants).

Other seizures without epilepsy include but are not limited to those induced by fever leading to febrile convulsions, metabolic disturbances such as hypoglycemia hyponatremia or hypoxia, substance withdrawal (e.g., GHB and derivatives thereof, benzos, ethanol and baclofen), eclampsia, binaural beat brainwave entertainment. Others are listed hereinbelow.

Thus, examples of neurological diseases and disorders include, without limitation, altered mental status, encephalopathy, stupor and coma, fever (febrile convulsions), cerebral palsy, cerebrovascular disease such as transient ischemic attack and stroke, demyelinating diseases such as multiple sclerosis, Guillain-Barré syndrome and chronic inflammatory demyelinating polyneuropathy (CIDP), epilepsy and seizure disorders, headache disorders such as migraine, cluster headache and tension headache, infections of the brain (encephalitis), brain meninges (meningitis), spinal cord (myelitis), movement disorders such as in Parkinson's disease, Huntington's disease, hemiballismus, tic disorder, and Gilles de la Tourette syndrome, CNS neoplasms (brain tumors), spinal cord tumors, PNS tumors, sleep disorders, speech and language disorders, spinal cord disorders such as tumors, infections, trauma, malformations (e.g., myelocele, meningomyelocele tethered cord), traumatic injuries to the brain, spinal cord and PNS, disorders of peripheral nerves, muscle (myopathy) and neuromuscular junctions, deafferentation pain (also called phantom pain, anesthesia dolorosa or denervation pain), various infections of the PNS such as botulism.

Examples of psychiatric diseases and disorders include, without limitation, psychotic disorders or diseases such as schizophrenia, anxiety disorders, dissociative disorders, personality disorders, mood disorders such as depression, affective disorders including unipolar and bipolar disorders, boarder line disorders and mental diseases or disorders.

Examples of neurodegenerative diseases and disorders include, without limitation, Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy (MSA), Parkinson's disease, Pelizaeus-Merzbacher Disease, Pick's disease, Primary lateral sclerosis, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, and Steele-Richardson-Olszewski disease.

The neurological disease or disorder, according to some embodiments of the present invention, is selected from the group consisting of epilepsy, convulsions, and seizure disorders, spasticity, skeletal muscle spasms, restless leg syndrome, anxiety, stress, multiple sclerosis, stroke, head trauma, spinal cord injury, (ALS), Parkinson's Disease, Huntington's Disease, Alzheimer's Disease, amyotrophic lateral sclerosis, neuropathic pain, myoclonus, schizophrenia, migraine, headaches and bipolar disorders. According to some embodiments of the present invention, the compounds described herein are utilized for treating epilepsy.

According to other embodiments of the present invention, the compounds described herein are utilized for treating epilepsy, other types of seizures, neuropathic pain and a bipolar disorder.

As discussed hereinabove, (2-ethyl-3-methyl-pentanoyl)-urea, which is referred to herein as Compound 4 or VCU (see, Table 1 hereinbelow), has been previously described as a minor tranquilizer and anti-anxiety agent, and was further studied by Goldstein et al. [22] as an aid for sleep disorders. Hence, the use of (2-ethyl-3-methyl-pentanoyl)-urea (Compound 4 or VCU, as a racemate) as a compound which can be used to treat anxiety and sleep disorders is excluded from the scope of the present embodiments.

Nonetheless, the advantageous use of purified stereoisomers of VCU, purified diastereoisomers in particular, has never been suggested.

Thus, according to another aspect of the present invention, there is provided a pharmaceutical composition packaged in a packaging material and identified in print, in or on the packaging material, for use in the treatment of a neurological disease or disorder, the composition includes at least one pure (isolated) stereoisomer of (2-ethyl-3-methyl-pentanoyl)-urea as presented herein.

According to yet another aspect of the present invention there is provided a method of treating a medical condition associated with a neurological disorder, the method is effected by administering to a subject in need thereof a therapeutically effective amount of at least one pure (isolated) stereoisomer of (2-ethyl-3-methyl-pentanoyl)-urea as presented herein.

According to still another aspect of the present invention there is provided a use of at least one pure (isolated) stereoisomer of (2-ethyl-3-methyl-pentanoyl)-urea, in the manufacture of a medicament for the treatment of a neurological disease or disorder.

As used herein, the phrase "therapeutically effective amount" describes an amount of the compound being administered which will relieve to some extent one or more of the symptoms of the condition being treated.

As demonstrated in the examples section that follows, an exemplary therapeutically effective amount of the compounds presented herein ranges between about 0.1 mg/kg body and about 100 mg/kg body. Alternatively, the therapeutically effective amount ranges from about 5 mg/kg body to about 70 mg/kg body, and according to other embodiments of the present invention the therapeutically effective amount ranges from about 10 mg/kg body to about 40 mg/kg body.

As used herein throughout the term "about" refers to ±10%.

In any of the methods and uses described herein, the acyl-urea containing compounds of the present embodiments can be utilized either per se or as a part of a pharmaceutical composition that further comprises a pharmaceutically acceptable carrier.

The compounds described hereinabove under Formula I, as defined hereinabove, can be utilized either per se or form a part of a pharmaceutical composition, which further comprises a pharmaceutically acceptable carrier.

Thus, according to another aspect of the present invention, there is provided a pharmaceutical composition which comprises, as an active ingredient, any of the compounds described hereinabove under Formula I and a pharmaceutically acceptable carrier. Some compounds according to this aspect of the present invention are Compound 1 and Compound 2, as presented in the Examples section that follows.

Correspondingly, according to additional aspects of the present invention, there is provided pharmaceutical composition, which comprises one or more compounds having the general Formulae II and III, as defined hereinabove, and a pharmaceutically acceptable carrier.

Additionally, there is provided a pharmaceutical composition which comprises one or more of the pure (isolated) stereoisomer of (2-ethyl-3-methyl-pentanoyl)-urea as presented herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

As mentioned hereinabove, the present inventors have shown in vivo therapeutic activity in animal models for Status Epilepticus (SE), other chemically-induced convulsion and/or seizure disorders, fever related and other febrile convulsion conditions, a metabolic disturbance and a substance withdrawal condition, as presented in the Examples section that follows. Such a therapeutic activity renders these compounds suitable for use as therapeutically active agents for the treatment of neurological diseases and disorders which involve chemically-induced seizures and other involuntary convulsions and other chronic conditions such as SE, as defined and discussed herein.

Based on the therapeutic activity exhibited by these compounds, according to another aspect of the present invention there is provided a use of the acyl-urea containing compounds, represented in the general Formulae II and III as presented hereinabove, as well enantiomers, diastereomers, hydrates, solvates or pharmaceutically acceptable salts thereof, as defined hereinabove, in the preparation of a medicament for the treatment of a neurological disease or disorder selected from the group consisting of status epilepticus (SE), a chemically-induced convulsions and/or seizure disorder, a febrile convulsion condition, a metabolic disturbance and a substancesustenancc withdrawal condition.

As demonstrated in the examples section that follows, an exemplary therapeutically effective amount of the compounds presented herein ranges between about 0.1 mg/kg body and about 100 mg/kg body. According to some embodiments, the therapeutically effective amount ranges from about 5 mg/kg body to about 70 mg/kg body, and according to other embodiments the therapeutically effective amount ranges from about 10 mg/kg body to about 40 mg/kg body.

An exemplary compound according to the present embodiments, namely (2-ethyl-3-methyl-pentanoyl)-urea (VCU, Compound 4), belonging to the family of compounds falling under Formula II, has been shown to have a protective effect against chemically-induced convulsions, as demonstrated in the Examples section that follows. Hence, according to some embodiments of the present invention, the compositions, methods or uses presented herein which are directed at treating status epilepticus (SE), a chemically-induced convulsions and/or seizure disorder, a febrile convulsion condition, a metabolic disturbance and a substance withdrawal condition, utilize compounds having the general Formula II.

According to some embodiments of the present invention, each of $R_2$-$R_4$ is hydrogen. Further according to some embodiments of the present invention, $R_1$ is ethyl, and according to other embodiments, Rb is ethyl and Ra is methyl or Rb is methyl and Ra is ethyl.

Such compounds defined in the above embodiments result in (2-ethyl-3-methyl-pentanoyl)-urea (VCU, Compound 4, see Table 1 hereinbelow) which possesses two chiral centers.

The advantageous use of a racemate of VCU or purified stereoisomers of VCU, purified diastereoisomers in particular, against status epilepticus and/or other chemically-induced seizures has never been suggested. Thus, according to some embodiments of the present invention, the preparations of a medicament, methods and/or compositions presented herein utilize a racemic mixture or a pure (isolated) stereoisomer of (2-ethyl-3-methyl-pentanoyl)-urea wherein the stereo-configuration at positions 2 and/or 3 is selected from the group consisting of an R-configuration, an S-configuration or a combination thereof. More specifically, the stereoisomer of (2-ethyl-3-methyl-pentanoyl)-urea include ((2S)-2-ethyl-(3S)-3-methyl-pentanoyl)-urea, ((2S)-2-ethyl-(3R)-3-methyl-pentanoyl-urea, ((2R)-2-ethyl-(3S)-3-methyl-pentanoyl-urea and ((2R)-2-ethyl-(3R)-3-methyl-pentanoyl-urea.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a neurological disease or disorder, as is detailed hereinabove.

Thus, according to an embodiment of the present invention, the pharmaceutical composition of the present invention is being packaged in a packaging material and identified in print, in or on the packaging material, for use in the treatment of a neurological disease or disorder, as is defined hereinabove.

According to some embodiments of the present invention, in any of the methods, uses and compositions presented herein pertaining to the compounds falling under the general Formula II, some compounds are those wherein each of $R_2$-$R_4$ is hydrogen, and other are compounds wherein each of $R_2$-$R_4$ is hydrogen and Rb is methyl.

In one embodiment each of $R_2$-$R_4$ is hydrogen, Rb is methyl, and each of Ra and $R_1$ is ethyl, resulting in the compound 1-(2-ethyl-3-methylpentanoyl)urea which is referred to hereinbelow as VCU or Compound 4, as discussed hereinabove demonstrated in the Examples section that follows.

Another one of the compounds wherein each of $R_2$-$R_4$ and Rb is hydrogen, Ra is propyl and $R_1$ is ethyl, resulting in the compound 1-(2-ethylhexanoyl)urea which is referred to hereinbelow as Compound 5, as demonstrated in the Examples section that follows.

Another compound wherein each of $R_2$-$R_4$ and Rb is hydrogen, Ra is ethyl and $R_1$ propyl is, resulting in the compound 1-(2-propylpentanoyl)urea which is referred to hereinbelow as Compound 6, as demonstrated in the Examples section that follows.

Another one of the compounds wherein each of $R_2$-$R_4$ and $R_1$ is hydrogen, and each of Ra and Rb is methyl, resulting in the compound 1-(3-methylbutanoyl)urea which is referred to hereinbelow as Compound 7, as demonstrated in the Examples section that follows.

Another one of the compounds wherein each of $R_2$-$R_4$ and Ra is hydrogen, and each of Rb and $R_1$ is methyl, resulting in the compound 1-(3-methylbutanoyl)urea which is referred to hereinbelow as Compound 8, as demonstrated in the Examples section that follows.

Similarly, according to some embodiments of the present invention, in any of the methods, uses and compositions presented herein pertaining to the compounds falling under the general Formula III, $R_2$-$R_4$ independently hydrogen.

According to further embodiments of the present invention, in any of the methods, uses and compositions presented herein, the compounds can be combined with other active ingredients which are commonly used to treat neurological diseases and disorders. Examples include, without limitation, carbamazepine (Tegretol), clobazam (Frisium), clonazepam (Klonopin), diazepam (Valium), ethosuximide (Zarontin), felbamate (Felbatol), fosphenyloin (Cerebyx), flurazepam (Dalmane), gabapentin (Neurontin), lamotrigine (Lamictal), levetiracetam (Keppra), lorazepam (Ativan), oxcarbazepine (Trileptal), mephenyloin (Mesantoin), phenobarbital (Luminal), phenyloin (Dilantin), pregabalin (Lyrica), paraldehyde (Paral), pentobarbital (Nembutal), primidone (Mysoline), valproic acid (Depakene, Convulex), sodium valproate (Epilim), tiagabine (Gabitril), topiramate (Topamax), valproate semisodium (Depakote, Epival) and vigabatrin (Sabril).

According to yet another aspect of the present invention there is provided a process of preparing the novel compounds presented herein, falling under Formula I, the process is effected by:

reacting a compound having the general Formula IV:

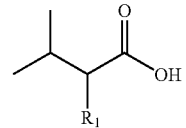

Formula IV wherein $R_1$ is hydrogen or an alkyl having from 1 to 10 carbon atoms, with a compound having the general Formula V:

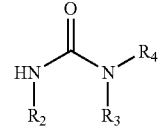

Formula V wherein $R_2$-$R_4$ are each independently hydrogen or an alkyl having from 1 to 10 carbon atoms, thereby obtaining the compounds.

It is note that since there is an option to have compounds having the general Formula IV with at least one chiral center at position-2, the scope of the present embodiments encompasses all stereoisomers of the compound having the general Formula IV, including isolated forms or any racemic mixtures thereof.

Excluded from the scope of this aspect of the present invention are compounds having the general Formula I, which result from reacting compounds having the general Formula V wherein each of $R_2$-$R_4$ is hydrogen, with compounds having the general Formula IV wherein $R_1$ is an alkyl having from 3 to 10 carbon atoms.

According to some embodiments, compound having the general Formula IV is converted into a reactive carboxylic derivative thereof. Alternatively the reactive carboxylic derivative is an acyl-halide.

The phrase "reactive carboxylic derivative", as used herein, refers to a derivative of a carboxylic acid or a carboxylate group which more reactive than the parent carboxylic acid group, such as, for example, a an acyl-halide an anhydride, a carboxylic ester or an amide, which are more reactive than their corresponding carboxylic acid.

The term "carboxylic acid", as used herein, refers to an R'—C(=O)—OH group, where R' is as defined herein.

The term "carboxylate", as used herein, refers to an R'—C(=O)—OR" group, where R' and R" are as defined herein.

According to some embodiments, the process is further effected by obtaining the compound having general Formula IV by reacting isovaleric acid with an alkylating agent having the general Formula VI:

R₁—X    Formula VI.

The phrase "alkylating agent", as used herein, refers to a chemical reagent which use thereof can place an alkyl, as this is define herein, at a designated position on a given reactant compound.

Examples of known alkylating agents include, without limitation, an alkylsulfonate, an alkyleneimine, phosgene, alkyl tosylates such as methyl tosylate, alkyl triflates such as methyl triflate, alkyl halides such as methyl bromide and methyl iodide, trimethyloxonium tetrafluoroborate, dialkyl sulfate, alumoxanes, trialkylaluminum and tris(trialkylyl)aluminum.

According to further aspects of the present invention there is provided a process of preparing isolated stereoisomers of (2-ethyl-3-methyl-pentanoyl)-urea (VCU), essentially as described in the Example section that follows below.

In essence, (2R)-ethyl-(3R)-methyl-valnoctic acid, (2S)-ethyl-(3S)-methyl-valnoctic acid, (2R)-ethyl-(3S)-methyl-valnoctic acid and (2S)-ethyl-(3R)-methyl-valnoctic acid are prepared as described in U.S. Pat. No. 6,417,399, using the corresponding starting materials, L-isoleucine or D-isoleucine, and are thereafter reacted with thionylchloride to thereby obtain the acyl-chloride of each of the four diastereomers, the acyl-chloride is thereafter reacted with urea to afford the enantiomerically pure (isolated) stereoisomers of (2-ethyl-3-methyl-pentanoyl)-urea.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Example 1

Chemical Syntheses

Materials and Methods:
Lithium diisopropylamine, n-butyl lithium, isovaleric acid, hexamethylphosphoramide, urea, 1-iodopropane, 2-iodopropane and t-butylacetylchloride were obtained from Sigma-Aldrich Israel Ltd.

Melting point was measured using Buchi 530 Capillary melting point apparatus.

NMR measurements were performed using Varian mercury series NMR 300 spectrometer.

GC-MS measurements were performed using HP 5890 series II GC equipped with a Hewlett-Packard ms engine (HP5989A) single quadropole, MS spectrometer, HP7673 auto-sampler, HP MS-DOS Chemstation and HP-5MS capillary column (0.25 μm×15 m×0.25 mm). Elemental analysis was performed using a 2400-2 Perkin-Elmer C, H, N analyzer, and an acceptance threshold of ±0.4 of theoretical values.

Preparation of
N-(2-isopropyl-2-substituted-acetyl)urea (Formula I)

General Procedure

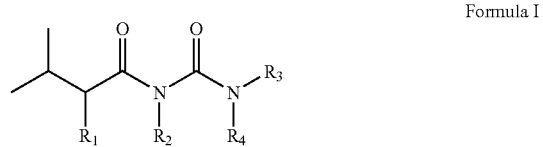

Formula I

A solution of lithium diisopropylamine (0.126 moles) in anhydrous THF (70 ml) is added to a dry flask and maintained under nitrogen atmosphere. After cooling the mixture to −15° C., n-butyl lithium (0.126 moles) in hexane solution is added slowly to the reaction mixture. Isovaleric acid (0.06 moles) is added dropwise while maintaining the temperature below 0° C. and the reaction mixture is stirred for 15 minutes. Thereafter, hexamethylphosphoramide (HMPA, 0.06 moles) is added rapidly and the reaction is completed by stirring at room temp for 30 minutes.

An alkyl halide (0.12 moles) is added rapidly at 0° C. and the reaction is completed by stirring for 1 hour at room temperature.

The product is isolated by acidification to pH 1-2 with ice-cold 10% HCl (150 ml), followed by extractions with petroleum ether. The combined organic layers are washed three times with 10% HCl, water and brine, dried over sodium sulfate and the solvent is evaporated under reduced pressure after filtration to obtain the crude product at a typical yield of 98%.

The general procedure for obtaining 2-isopropyl-2-substituted-acetic acid is illustrated in Scheme 1 below.

Scheme 1

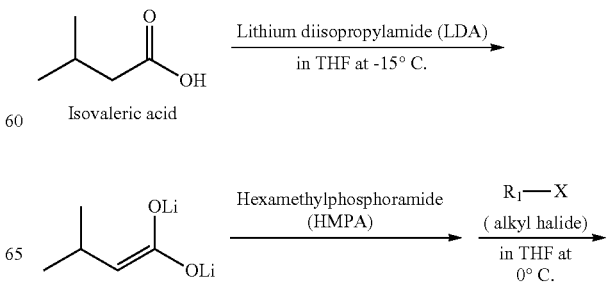

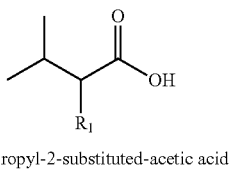

2-isopropyl-2-substituted-acetic acid

An acyl halide of 2-isopropyl-2-substituted-acetic acid, namely 2-isopropyl-2-substituted-acetyl chloride, is obtained by using thionyl chloride (SOCl$_2$) according to Furniss et al. [24]. 2-Isopropyl-2-substituted-acetyl chloride (0.03 moles) dissolved in dry acetonitrile (50 ml) is added slowly to a stirred and boiling solution of urea or an urea derivative (0.08 mole) in dry acetonitrile (150 ml) and the reaction mixture is refluxed for two hours. Thereafter the organic solvent is evaporated under reduced pressure and the product is dissolved in ethyl acetate (100 ml) and washed three times with 10 ml of distilled water. The organic fraction is dried over MgSO$_4$, filtered and evaporated under reduced pressure. The product is purified by crystallization using an ethyl acetate:petroleum ether mixture (1:3), typically affording white crystals at a typical yield of 85%.

The general procedure for obtaining a compound having the general Formula I from 2-isopropyl-2-substituted-acetic acid is illustrated in Scheme 2 below.

Scheme 2

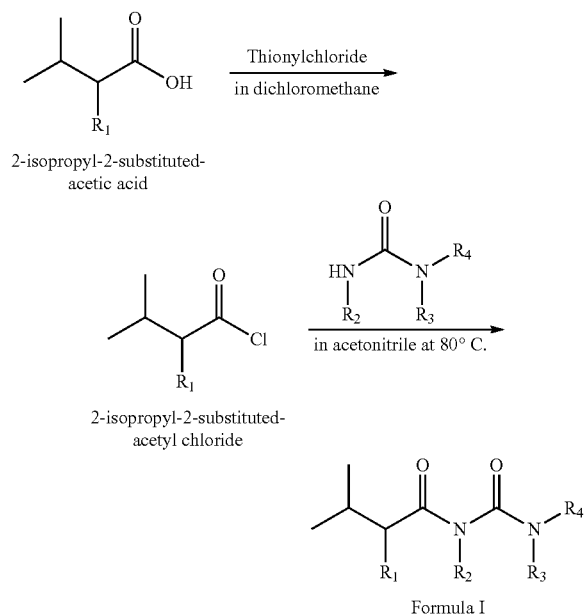

Preparation of N-(2-isopropyl-2-propyl-acetyl)urea (Compound 1, PIU)

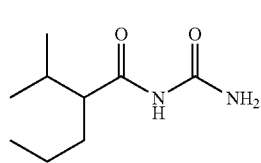

Compound 1 (PIU)

N-(2-Isopropyl-2-propyl-acetyl)urea (Compound 1) was prepared according to the general procedure presented hereinabove for obtaining compounds having the general Formula I, using 1-iodopropane for an alkyl halide and urea.

Pure 2-isopropyl-2-propyl-acetic acid was obtained after distillation at a boiling point of 125° C. under reduced pressure (30 mm Hg).

Compound 1 was obtained at an overall yield of 71% as white crystals which exhibited a melting point of 213° C., the chemical structure thereof was confirmed by spectroscopic methods (NMR and GC-MS), and its purity was established by elemental analysis.

MS-EI, m/z: 144, 129, 115, 72, 61.

$^1$H NMR (300 MHz, DMSO-d$_6$): 0.78-0.88 (m, 9H), 1.06-1.22 (m, 2H), 1.28-1.54 (m, 2H), 1.62-1.74 (m, 1H), 2.1-2.2 (m, 1H), 7.21 (s, 1H), 7.86 (s, 1H), 10.14 (s, 1H).

Elemental analysis (C, H, N): C$_9$H$_{18}$N$_2$O$_2$.

Preparation of optically active N-(2-isopropyl-2-propyl-acetyl)urea (R-PIU and S-PIU)

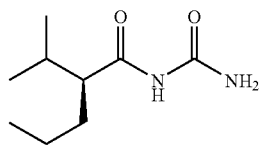

R-PIU

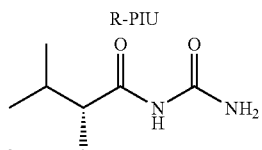

R-PIU

The optically active, or enantiomerically pure (R)-2-isopropyl-2-propyl-acetic acid (R-PIA) and (S)-2-isopropyl-2-propyl-acetic acid (S-PIA) were prepared according to published procedures [25]. Briefly, the enantioselective synthesis of 2-isopropyl-2-propyl-acetic acid (PIA) enantiomers was achieved by conversion of valeric acid to acylchloride followed by coupling of valeroylchloride with optically pure (4S)- and (4R)-benzyl-2-oxazolidinones chiral auxiliary in order to prepare (4S)- and (4R)-3-(1'-oxopentyl)-4-benzyl-2-oxazolidinones respectively. The two oxazolidinone enolates were alkylated using isopropyltriflate to obtain (4S,2'R)- and (4R,2'S)-3-(2'-isopropyl-1'-oxopentyl)-4-benzyl-2-oxazolidinones respectively, which were further hydrolyzed using lithium hydroperoxide to yield R-PIA and S-PIA enantiomers respectively with optical purity (enantiomeric excess) above 99.4%.

The successive conversions of R-PIA and S-PIA to the respective amides and urea derivatives were accomplished as described in the previous example for racemic PIU.

Preparation of N-(2,2-Diisopropyl-acetyl)urea (Compound 2, DIU)

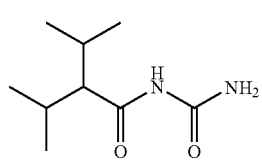

Compound 2 (DIU)

N-(2,2-Diisopropyl-acetyl)urea (Compound 2) was prepared according to the general procedure presented hereinabove for obtaining compounds having the general Formula I, using 2-iodopropane for an alkyl halide and urea.

Compound 2 was obtained at an overall yield of 51% as white crystals which exhibited a melting point of 199-200° C., the chemical structure thereof was confirmed by spectroscopic methods (NMR and GC-MS), and its purity established by elemental analysis.

MS-EI: m/z=144, 129, 86, 69, 61.

$^1$H NMR (300 MHz, CDCl$_3$ δ TMS): 0.91-0.98 (t, J=0.02, 12H), 1.78-1.84 (t, J=0.02, 1H), 1.98-2.1 (m, 2H), 5.49 (s, 1H), 8.41 (s, 1H), 8.9 (s, 1H).

Elemental analysis (C, H, N): C$_9$H$_{18}$N$_2$O$_2$.

Preparation of N-(t-butyl-acetyl)urea (Formula II)

General Procedure

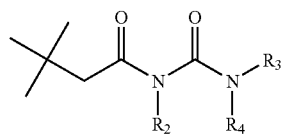

Formula II

Urea or a urea derivative (0.045 moles) is dissolved in dry acetonitrile (40 ml) and refluxed for one hour, followed by the addition of tert-butylacetylchloride (0.018 moles, Sigma-Aldrich Israel Ltd.) dissolved in acetonitrile (7 ml). The reaction mixture is stirred for additional two hours, the organic solvent is thereafter evaporated under reduced pressure and the residue is dissolved in ethyl acetate (20 ml), washed three times with distilled water, 1N NaOH solution and brine, and adjusted to a neutral pH. The organic fraction is dried over MgSO$_4$, filtered and evaporated under reduced pressure.

The product is purified by crystallization using an ethyl acetate:petroleum ether mixture (1:3), typically affording white crystals at a typical yield of 89%.

The general procedure for obtaining a compound having the general Formula II from tert-butylacetylchloride is illustrated in Scheme 3 below.

Scheme 3

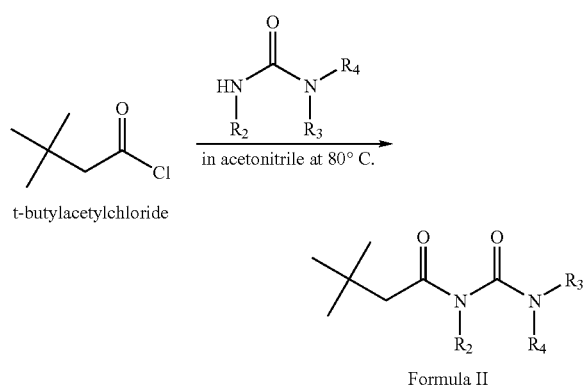

Formula II

Preparation of N-(t-butyl acetyl)urea (Compound 3, TBU)

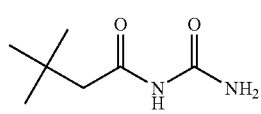

Compound 3 (TBU)

N-(t-Butyl acetyl)urea (Compound 3) was prepared according to the general procedure presented hereinabove for obtaining compounds having the general Formula II, using urea.

Compound 3 was obtained in an overall yield of 51% as white crystals which exhibited a melting point of 174-175° C., the chemical structure thereof was confirmed by spectroscopic methods (NMR, GC-MS and IR), and its purity established by elemental analysis.

MS-EI, m/z: 143, 102, 83, 59, $^1$H NMR (300 MHz, CDCl$_3$ δ TMS): 1.044 (s, 9H), 2.191 (s, 2H), 5.67 (s, 1H), 8.371 (s, 1H), 9.532 (s, 1H).

Elemental analysis (C, H, N): C$_7$H$_{14}$N$_2$O$_2$.

Preparation of 1-(2-ethyl-3-methyl-pentanoyl)-urea (Compound 4, VCU)

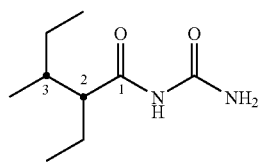

Compound 4 (VCU)

A solution of 0.126 mole of lithiumdiisopropylamine (LDA) prepared by dissolving diisopropylamine in dry tetrahydrofuran under nitrogen. Thereafter the mixture cooled to −20° C. and butyl lithium (BuLi, 0.126 moles) was added slowly. After completing the addition of BuLi, the reaction mixture was stirred at 0° C. for 30 minutes.

The LDA solution was cooled again to −20° C. followed by addition of 3-methylpentanoic acid (0.06 moles). After completing the addition of the carboxylic acid, the mixture was stirred for 15 minutes and a solution of HMPA (0.06 mole) was added rapidly to the reaction mixture and stirred for 5 minutes at 4° C. to form the corresponding enolate.

Following the enolate formation, ethyliodide (0.12 moles) was added drop wise to the reaction mixture at 0° C. and stirred for 1 hour at room temperature. After the reaction was completed, the reaction mixture was acidified to pH 1-2 using 10% HCl and the product was extracted three times with 300 ml of petroleum ether. The combined petroleum ether fractions was washed with HCl (1N), water and brine, dried over sodium sulfate and filtered. The solvent evaporated under reduced pressure to yield pure branched carboxylic acids.

2-Ethyl-3-methyl-pentanoylchloride (0.057 mol), was prepared using thionylchloride according to a published method [24], and dissolved in dry acetonitrile (50 ml). The 2-ethyl-3-methyl-pentanoylchloride solution was slowly added to a boiling solution of urea (0.14 moles) in dry acetonitrile (100 ml) and was allowed to reflux for 2 hours. Thereafter the organic solvent was evaporated under reduced pressure and the product was dissolved in 100 ml ethyl acetate and washed three times with 20 ml of distilled water. The organic fraction was dried over MgSO$_4$, filtered and evaporated under reduced pressure. The product was purified by crystallization from ethyl acetate.

Compound 4 was obtained in an overall yield of 61% as white crystals which exhibited a melting point of 147-148° C., the chemical structure thereof was confirmed by spectroscopic methods (NMR and GC-MS), and its purity established by elemental analysis.

MS-EI, m/z: 130, 115, 87, 72, 61.

$^1$H NMR (300 MHz, CDCl$_3$ δ TMS): 0.86-0.96 (m, 9H), 1.08-1.24 (m, 1H), 1.38-1.74 (m, 4H), 1.96-2.06 (m, 1H), 5.35 (s, 1H), 8.37 (s, 1H), 8.7 (s, 1H)

Elemental analysis (C, H, N): C$_9$H$_{18}$N$_2$O$_2$.

Preparation of pure diastereomers of 1-(2-ethyl-3-methyl-pentanoyl)-urea

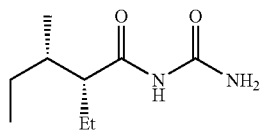
(2R, 3S)-VCU

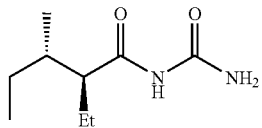
(2R, 3R)-VCU

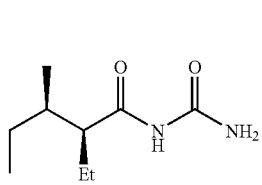
(2S, 3S)-VCU (2S, 3R)-VCU

The synthesis of pure diastereomers of VCU is executed substantially as described in U.S. Pat. No. 6,417,399, as illustrated in Schemes 4, 5 and 6 below.

Scheme 4

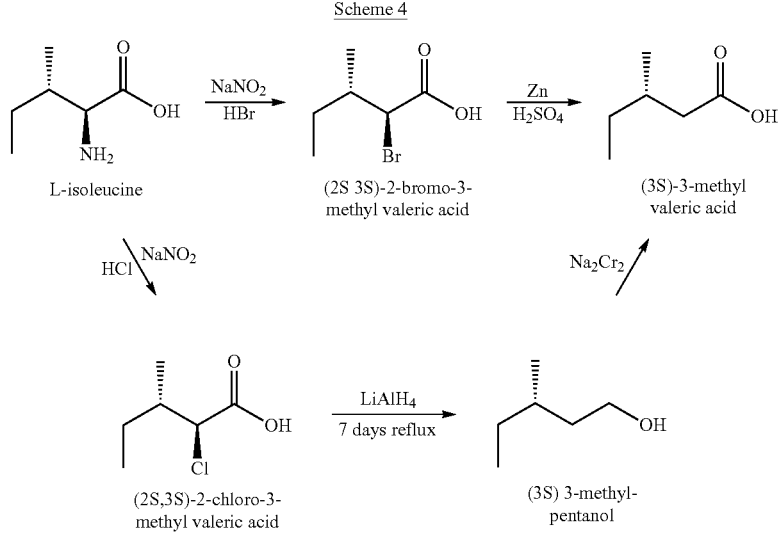

Scheme 4 presents the synthetic path for obtaining (3S)-3-methyl valeric acid, starting from L-isoleucine.

Scheme 5

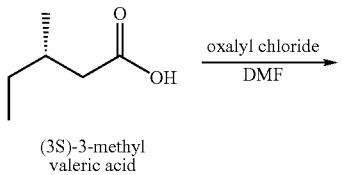

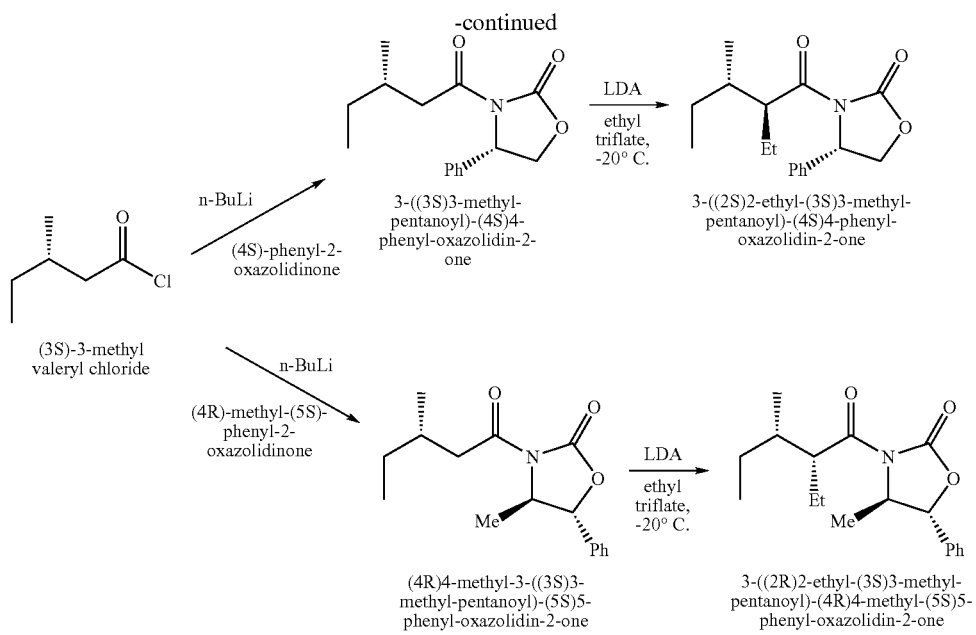

Scheme 5 presents the synthetic paths starting from (3S)-3-methyl valeric acid and diverging into two of the possible diastereomers of VCU, namely (2S)ethyl(3S)methyl and (2R)ethyl(3S)methyl forms.

Scheme 6

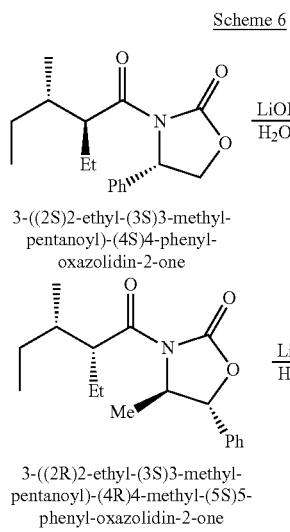

Scheme 6 presents the parallel synthetic paths which afford two diastereomers of valnoctic acid, (2S)-ethyl-(3S)-methyl-valnoctic acid and (2R)-ethyl-(3S)-methyl-valnoctic acid.

(2R)-Ethyl-(3R)-methyl-valnoctic acid and (2S)-ethyl-(3R)-methyl-valnoctic acid are prepared in a similar process, using the corresponding starting materials, D-isoleucine, (4R)-benzyl-2-oxazolidinone and (4R,3'R)-3-(3'-methyl-1'-oxopentyl)-4-benzyl-2-oxazolidinone.

The acyl-chloride of each of the four diastereomers of valnoctic acid, namely (2S)-ethyl-(3S)-methyl-valnoctic acid, (2R)-ethyl-(3S)-methyl-valnoctic acid, (2R)-ethyl-(3R)-methyl-valnoctic acid and (2S)-ethyl-(3R)-methyl-valnoctic acid (0.057 mol), are prepared by coupling of thionyl-chloride and the corresponding valnoctic acid diastereomer according to a published method [24]. The valnoctyl-chloride is dissolved in dry acetonitrile (50 ml), and the resulting solution is slowly added to a boiling solution of urea (0.14 mole) in dry acetonitrile (100 ml) and allowed to reflux for 2 hours. Thereafter the organic solvent is evaporated under reduced pressure and the product is dissolved in ethyl acetate (100 ml) and washed three times with 20 ml of distilled water. The organic fraction is dried over MgSO4, filtered and evaporated under reduced pressure. The products are purified by crystallization from ethyl acetate.

Preparation of 1-(2-ethyl-hexanoyl)-urea (Compound 5, EBU)

Compound 5 (EBU)

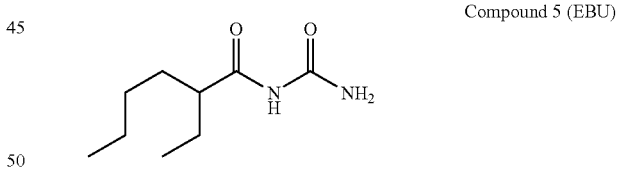

2-Ethyl-hexanoylchloride (0.057 mol, Sigma-Aldrich Israel Ltd.), dissolved in dry acetonitrile (50 ml), was slowly added to a dry, boiling solution of urea (0.14 mole) in acetonitrile (100 ml) and allowed to reflux for 2 hours. Thereafter the organic solvent was evaporated under reduced pressure and the product was dissolved in ethyl acetate (100 ml) and washed three times with 20 ml of distilled water. The organic fraction was dried over $MgSO_4$, filtered and evaporated under reduced pressure. The product was purified by crystallization from ethyl acetate.

Compound 5 was obtained in an overall yield of 61% as white crystals which exhibited a melting point of 158-159° C., the chemical structure thereof was confirmed by spectroscopic methods (NMR and GC-MS), and its purity established by elemental analysis.

MS-EI, m/z: 158, 130, 115, 87, 72, 61, 57.

$^1$H NMR (300 MHz, CDCl$_3$ δ TMS): 0.848-0.929 (m, 6H), 1.209-1.69 (m, 8H), 2.133-2.209 (m, 1H), 5.543 (s, 1H), 8.392 (s, 1H), 9.255 (s, 1H).

Elemental analysis (C, H, N): C$_9$H$_{18}$N$_2$O$_2$.

Preparation of 1-(2-propyl-pentanoyl)-urea (Compound 6, VPU)

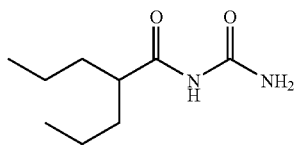

Compound 6 (VPU)

Valproyl chloride (0.057 mol), prepared by coupling of thionylchloride and valproic acid according to a published method [24], was dissolved in dry acetonitrile (50 ml), and the resulting solution was slowly added to a boiling solution of urea (0.14 mole) in dry acetonitrile (100 ml) and allowed to reflux for 2 hours. Thereafter the organic solvent was evaporated under reduced pressure and the product was dissolved in ethyl acetate (100 ml) and washed three times with 20 ml of distilled water. The organic fraction was dried over MgSO$_4$, filtered and evaporated under reduced pressure. The products were purified by crystallization from ethyl acetate.

Compound 6 was obtained in an overall yield of 83% as white crystals which exhibited a melting point of 217-220° C., the chemical structure thereof was confirmed by spectroscopic methods (NMR and GC-MS), and its purity established by elemental analysis.

MS-EI, m/z: 144, 129, 115, 72, 61.

$^1$H NMR (300 MHz, CDCl$_3$ δ TMS): 0.86-0.94 (t, J=0.05, 6H), 1.2-1.74 (m, 8H), 2.24-2.4 (m, 1H), 5.62 (s, 1H), 8.4 (s, 1H), 9.42 (s, 1H).

Elemental analysis (C, H, N): C$_9$H$_{18}$N$_2$O$_2$.

Preparation of 3-methylbutanoylurea (Compound 7)

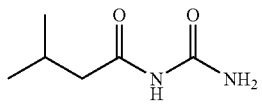

Compound 7

Isovaleryl chloride (0.057 mol, Sigma-Aldrich Israel Ltd.), dissolved in dry acetonitrile (50 ml), was slowly added to a boiling solution of urea (0.14 mole) in dry acetonitrile (100 ml) and allowed to reflux for 2 hours. Thereafter the organic solvent was evaporated under reduced pressure and the product was dissolved in ethyl acetate (100 ml) and washed three times with 20 ml of distilled water. The organic fraction was dried over MgSO$_4$, filtered and evaporated under reduced pressure. The product was purified by crystallization from ethyl acetate.

Compound 7 was obtained at an overall yield of 71% as white needles which exhibited a melting point of 206-208° C., the chemical structure thereof was confirmed by spectroscopic methods (NMR and GC-MS), and its purity established by elemental analysis.

MS-EI, m/z: 129, 102, 85, 61, 59.

$^1$H NMR (300 MHz, CDCl$_3$ δ TMS): 0.977-0.999 (d, J=0.022, 6H), 2.09-2.209 (m, 3H), 5.237 (s, 1H), 8.252 (s, 1H), 8.392 (s, 1H).

Elemental analysis (C, H, N): C$_9$H$_{18}$N$_2$O$_2$.

Preparation of 2-methylbutanoylurea (Compound 8)

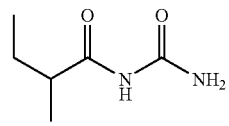

Compound 8

2-Methylbutyryl chloride (0.057 mol, Sigma-Aldrich Israel Ltd.), dissolved in dry acetonitrile (50 ml), was slowly added to a boiling solution of urea (0.14 mole) in dry acetonitrile (100 ml) and allowed to reflux for 2 hours. Thereafter the organic solvent was evaporated under reduced pressure and the product was dissolved in ethyl acetate (100 ml) and washed three times with 20 ml of distilled water. The organic fraction was dried over MgSO$_4$, filtered and evaporated under reduced pressure. The products were purified by crystallization from ethyl acetate.

Compound 8 was obtained at an overall yield of 68% as white needles which exhibited a melting point of 178-180° C., the chemical structure thereof was confirmed by spectroscopic methods (NMR and GC-MS), and its purity established by elemental analysis.

MS-EI, m/z: 129, 116, 73, 57, 61, 57.

$^1$H NMR (300 MHz, CDCl$_3$ δ TMS): 0.905-0.954 (t, J=0.025, 3H), 1.165-1.188 (d, J=0.023, 3H), 1.441-1.748 (m, 2H), 2.269-2.339 (m, 1H), 5.391 (s, 1H), 8.33 (s, 1H), 8.959 (s, 1H).

Elemental analysis (C, H, N): C$_9$H$_{18}$N$_2$O$_2$.

Preparation of 2,2-dimethylpropanoylurea (Compound 9)

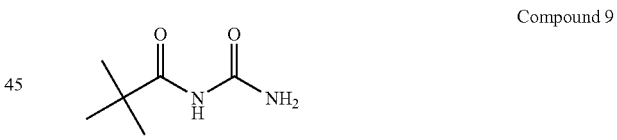

Compound 9

Tert-butyryl chloride (0.057 mol, Sigma-Aldrich Israel Ltd.), dissolved in dry acetonitrile (50 ml), was slowly added to a boiling solution of urea (0.14 mole) in dry acetonitrile (100 ml) and allowed to reflux for 2 hours. Thereafter the organic solvent was evaporated under reduced pressure and the product was dissolved in ethyl acetate (100 ml) and washed three times with 20 ml of distilled water. The organic fraction was dried over MgSO$_4$, filtered and evaporated under reduced pressure. The products were purified by crystallization from ethyl acetate.

Compound 9 was obtained at an overall yield of 75% as white needles which exhibited a melting point of 148-149° C., the chemical structure thereof was confirmed by spectroscopic methods (NMR and GC-MS), and its purity established by elemental analysis.

MS-EI, m/z: 144, 129, 89, 57.

$^1$H NMR (300 MHz, CDCl$_3$ δ TMS): 1.246 (s, 9H), 5.234 (s, 1H), 7.794 (s, 1H), 8.269 (s, 1H).

Elemental analysis (C, H, N): C$_6$H$_{12}$N$_2$O$_2$.

Table 1 below summarizes the compounds that were synthesized according to the above procedures.

TABLE 1

| Structure | Chemical Name | Abbreviation |
|---|---|---|
| (structure) | 1-(2-isopropyl-pentanoyl)urea | Compound 1 PIU |
| (structure) | R-1-(2-isopropyl-pentanoyl)urea | Compound 1R R-PIU |
| (structure) | S-1-(2-isopropyl-pentanoyl)urea | Compound 1S S-PIU |
| (structure) | 1-(2-isopropyl-3-methyl-butanoyl)urea | Compound 2 DIU |
| (structure) | 1-(3,3-dimethyl-butyryl)urea | (Compound 3) TBU |
| (structure) | 1-(2-ethyl-3-methyl-pentanoyl)-urea | Compound 4 VCU |
| (structure) | 1-(2-ethyl-hexanoyl)-urea | Compound 5 EBU |
| (structure) | 1-(2-propyl-pentanoyl)-urea or valproate urea | Compound 6 VPU |
| (structure) | 3-methyl-butanoylurea or isovaleroyl urea | Compound 7 |
| (structure) | 2-methyl-butanoylurea | Compound 8 |

TABLE 1-continued

| Structure | Chemical Name | Abbreviation |
|---|---|---|
| (structure) | 2,2-dimethyl-propanoylurea or 1-(pivaloyl)urea | Compound 9 |

Example 2

In-Vivo Studies

Anticonvulsant Activity Assays:

Exemplary compounds according to the present embodiments were tested for their ability to protect against chemically and electrically induced convulsions, in two models of epilepsy in mice and rats. In the first model, the maximal electroshock seizure test (MES) was used to show efficacy for antiepileptic agents against partial and generalized seizure type epilepsy, the common epilepsy among therapy resistant epileptic patients. In the second model, the subcutaneous metrazol test (scMet) was used to measure seizure threshold and was used as a standard screening procedure to show efficacy for agents against seizure threshold and absence seizures. The models and the biological activity protocols followed in the examples presented herein have been described in the art [23].

Briefly, Maximal Electroshock Seizure (MES) assay measures drug capacity to prevent seizure spread and is thus considered to model generalized tonic-clonic seizures. The assay was conducted using a supra-maximal current of 50 mA and 60 Hz for 0.2 seconds in mice, and 150 mA and 60 Hz for 0.2 seconds in rats. The current was delivered to the subjects by means of corneal electrodes to produce tonic hind limb extension. Animals not displaying tonic hind limb extension were considered affected positively by the tested compound.

Subcutaneous Metrazole Seizure Threshold Test (scMet) assay measures the ability of an agent to elevate seizure threshold and is considered to model generalized absence seizures. The assay was performed by subcutaneous injection of 85 mg/kg of the convulsant agent metrazole that induces clonic seizures in at least 97% of all animal models (rats and mice).

In a third model, the compounds were tested for their ability to block 6 Hz (32 mA) seizures following intraperitoneal administration thereof to male mice. This test is aimed at identifying new drug candidates for the treatment of therapy-resistant partial seizures.

Briefly, psychomotor seizure (6-Hz) assay measures the resistance of a subject to induced psychomotor seizures. The assay was conducted in mice which were pretreated with the test compound. At varying times after treatment, individual subjects were challenged with sufficient current of 32 mA at 6 Hz for 3 seconds, or 44 mA at 6 Hz for 3 seconds, delivered through corneal electrodes to elicit a psychomotor seizure. Animals which were not affected by the current were considered affected positively by the tested compound, thus compounds which were found active in this test are considered promising novel drug candidates for the treatment of therapy-resistant seizures.

Compounds were also tested in two other models: the Bicuculline (BIC) and Picrotoxin (PIC) assay and the hippocampal kindling screening assay, as described hereinbelow.

Thus, in a fourth model, Bicuculline (BIC) and Picrotoxin (PIC) were used to further investigate the anticonvulsant activity of the compounds presented herein. Bicuculline is a competitive antagonist of GABA A receptors, and thus induces an effect that mimics epilepsy. It is therefore widely utilized in the in vitro study of epilepsy, generally in cortical neurons in prepared brain slices from rodents. Picrotoxin, also known as cocculin, is a plant alkaloid which exhibits a strong non-competitive antagonist activity of GABA A receptors, and thus picrotoxin has a seizure simulative effect. Hence, BIC and PIC are chemoconvulsants that act by antagonizing GABA receptors and blocking chloride channels respectively, thereby inducing clonic seizures.

Briefly, the Bicuculline (BIC) and Picrotoxin (PIC) assay was conducted by administering the agents subcutaneously at a dosage of 2.7 mg/kg for BIC and 3.15 mg/kg for PIC at the previously determined time to peak effect for the test compound. Absence of a clonic seizure in the subject indicated that the test compound has the ability to protect against seizure threshold.

In a fifth model, the hippocampal kindling assay [23, 26] was used to identify new drug candidates effective for the treatment of difficult-to-control seizure types and complex partial seizures, as well as compounds that may be effective as mood stabilizer for treating bipolar disorder [26], and was conducted according to the protocol described therein.

Briefly, this test was conducted by using a bipolar stimulating electrode which was implanted in the hippocampus of rats, and the rats were kindled according to a described method [27]. One week after implantation of the electrodes, the rats were stimulated with supra-threshold trains of 200 μA and 50 Hz for 10 seconds every 30 minutes for 6 hours on alternate days until the animals were fully kindled. Animals were considered fully kindled when they displayed stable stage 5 seizures. The behavioral seizures were scored according to the following criteria ("seizure score"): stage 1—mouth and facial clonus; stage 2—stage 1 plus head nodding; stage 3—stage 2 plus forelimb clonus; stage 4—stage 3 plus rearing; and stage 5—stage 4 plus repeated rearing and falling.

For these studies, each of the compounds was evaluated for its ability to block the kindled motor seizure (seizure scores 4 and 5) and limbic behavioral seizures (seizure score between 1 and 3). Additionally the new drug candidate was evaluated for their ability to reduce after discharge duration. The term "after-discharge-duration" is the duration (measured in seconds) of the stages defined above, which are elicited by the electrical currents delivered to the rats. A promising drug candidate is one that can reduce the seizure score and the after-discharge-duration to a minimum, therefore the more potent the drug is, the lower is the seizure score and the shorter the after-discharge-duration are after drug administration.

At least one week after the fully kindled state was reached, a dose of the test compound was administered intraperitoneally and its effect on behavioral seizure score and after-discharge-duration following 200 μA stimulation was assessed at various time intervals before drug administration and after drug administration. Animals not displaying stage 4 or 5 were considered affected positively from seizure generalization.

Status Epilepricus (SE) Protection Assays:

Exemplary compounds according to the present embodiments were tested for their ability to protect against chemically induced convulsions, using a model of epilepsy in rats. The pilocarpine (see, chemical structure below) model of epilepsy was used to measure seizure threshold and was used as a standard screening procedure to show efficacy of the compounds presented herein against Status Epilepricus (SE) seizures. The models and the biological activity protocols followed in the examples presented herein have been described in the art [28]. This model shares many characteristics with nerve agent induced seizures since both initiation and early expression of nerve agent induced seizures are cholinergic followed by the recruitment of other neurotransmitter systems that serve to reinforce recurring seizure activity progressing to Status Epilepricus.

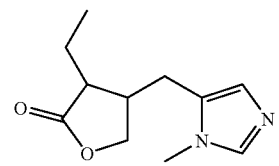

(3-ethyl-dihydro-4-((1-methyl-1H-imidazol-5-yl)methyl)furan-2(3H)-one)

The pilocarpine model is one of the most recognized animal models of SE. Briefly, the Pilocarpine Induced Epilepsy model (PIE) consists of systemic administration of the cholinergic agent and muscarinic agonist pilocarpine which induces spontaneous seizures in subjects after a latency of 14-15 days. Experiments presented in the art demonstrated that structural damage of the brain leads to spontaneous recurrent seizures. The characteristic of the seizure resembles human partial epilepsy. In rats, a behavior (akinesia, facial automatisms, limbic seizures consisting of forelimb clonus with rearing, salivation, masticatory jaw movements, and falling) and EEG changes (significant theta rhythm and isolated spikes in hippocampus, synchronization of the activity in hippocampus and cortex, EEG seizures, status epilepticus) can be observed and recorded.

The application of this model in rodents causes the induction of both fetal arid interictal activity in hippocampal and cortical regions of the brain. Clinical manifestations include ataxia, akinesia and facial automatisms where symptoms quickly progress to full SE lasting up to twelve hours. This protective activity can be correlated closely with electrographic changes, depending of the level of protection observed in the initial qualitative screen a series of evaluations using this chemoconvulsant may be employed to assess certain pharmacological characteristics of candidate compounds. Specifically, the effects of systematic administration of pilocarpine in rats promotes sequential behavioral and electrographic changes that can be divided in three distinct periods: (a) an acute period that built up progressively into a limbic status epilepticus and that lasts 24 hours, (b) a silent period with a progressive normalization of EEG and behaviour which varies from 4 to 44 days, and (c) a chronic period with spontaneous recurrent seizures (SRSs). The main features of the SRSs observed during the long-term period resemble those of human complex partial seizures and recurs 2-3 times per week per animal. Therefore, this experimental approach serves as a model of epilepsy mimicking the human condition.

Acute toxicity was determined by recording acute motor impairment after three doses of 30, 100 and 300 mg/kg of the tested compounds. The compounds were administered by the intraperitoneal (i.p.) route to three groups of 4 Sprague Dawley rats. The behavior of the animals was observed closely and recorded over a time period of two hours.

The ability to prevent the development of SE was determined by the administration of a minimally toxic dose of the tested compounds, given to male albino Sprague Dawley rats via the i.p. route of administration. Thereafter a challenging dose of pilocarpine (380 mg/kg) was administered after 0.25, 0.5, 1, 2, and 4 hours of treatment with the tested compounds. The results were used as an indication of the capacity to provide protection or lack thereof against chemically induced SE. The seizure severity was determined using the Racine scale [29].

The Racine scale was used to classify and quantify the effects according to the following stages:
Stage 1—mouth and facial tonus;
Stage 2—stage 1 plus head nodding;
Stage 3—stage 2 plus fore limb clonus;
Stage 4—stage 3 plus rearing; and
Stage 5—stage 4 plus repeated rearing and falling.

This capacity of a test compound to arrest pilocarpine-induced status was quantified by the dose of the tested compound which was calculated by statistical techniques to produce a characteristic effect in 97 percent of the subjects to whom the dose was given ($ED_{97}$). In addition, the 24 hours morbidity was also be determined after each test was completed.

Quantitative determination of the protective effects was measured for compounds which had significant qualitative protection. These tests included calculations of the peak time-response as well as determination of the effective dose ($ED_{50}$) and the toxic dose ($TD_{50}$). At least 10 potential doses with a minimum of 8 rats per dose were utilized in these calculations. Confidence limits and standard errors were provided for each candidate undergoing quantitative assessment.

Results of Anticonvulsant Activity Assays:

Table 2 presents the experimental results of the tests conducted in the scMet and MES rat models, according to which the median effective dose ($ED_{50}$) of Compound 1 was evaluated:

TABLE 2

| Test model | Dose (mg/kg) | Fraction of rats which responded to the treatment |
|---|---|---|
| scMet | 25 | 1/8 |
| scMet | 40 | 2/8 |
| scMet | 50 | 5/8 |
| scMet | 100 | 8/8 |
| MES | 6 | 0/8 |
| MES | 12 | 3/8 |
| MES | 25 | 6/8 |
| MES | 50 | 8/8 |

As can be seen in Table 2, Compound 1 clearly exhibited dose dependent anticonvulsant activity in rat-scMet model. The $ED_{50}$ (median effective dose) in the scMet model following oral administration to rats was 45 mg/kg with a 95% confidence interval of 35 to 61 mg/kg.

As can further be seen in Table 2, Compound 1 was also active in the rat-MES model, exhibiting an $ED_{50}$ of 16 mg/kg with a 95% confidence interval of 11 to 23 mg/kg.

Table 3 presents the experimental results of the tests conducted in the scMet and MES rat models, according to which the $ED_{50}$ of Compound 2 was evaluated:

TABLE 3

| Test model | Dose (mg/kg) | Fraction of rats which responded to the treatment |
|---|---|---|
| scMet | 6 | 1/8 |
| scMet | 12 | 2/8 |
| scMet | 25 | 6/8 |
| scMet | 50 | 8/8 |
| MES | 15 | 1/8 |
| MES | 30 | 5/8 |
| MES | 60 | 5/8 |
| MES | 120 | 8/8 |

As can be seen in Table 3, Compound 2 demonstrated excellent efficacy and dose dependent anticonvulsant activity in rat-scMet model, and exhibited an $ED_{50}$ of 16 mg/kg with a 95% confidence interval of 10 to 23 mg/kg.

As can further be seen in Table 3, Compound 2 also demonstrated efficacy in the rat-MES model, exhibiting an $ED_{50}$ of 33 mg/kg with a 95% confidence interval of 18 to 51 mg/kg.

Results disclosed in the art, which were measured in both the rat-scMet and the rat-MED models for the reference compounds N-(2,2,3,3-tetramethylcyclopropanecarbonyl)urea (see, Reference Compound 1 below) and N-(2,2,3,3-tetramethylcyclopropyl carbonyl)glycinamide (see, Reference Compound 2 below) as well as for valproic acid, are brought herein for comparison.

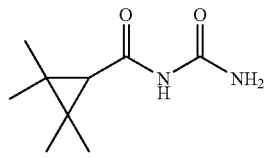

Reference Compound 1

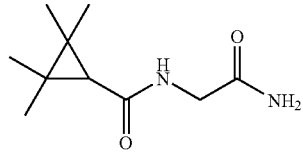

Reference Compound 2

In the rat-scMet model, Reference Compound 1 exhibited an $ED_{50}$ of 92 mg/kg with a 95% confidence interval of 50-151 mg/kg [6], while Reference Compound 2 was inactive at a dose of 250 mg/kg ($ED_{50}$ higher than 250 mg/kg) [30], and valproic acid showed an $ED_{50}$ of 646 mg/kg with a 95% confidence interval of 466 to 869 mg/kg in the rat-scMet model [23].

In the rat-MES model, Reference Compound 1 exhibited an $ED_{50}$ of 29 mg/kg with a 95% confidence interval of 18 to 47 mg/kg [6], while Reference Compound 2 exhibited an $ED_{50}$ of 73 mg/kg [30]. Valproic acid was significantly less active than the compounds presented herein, exhibiting an $ED_{50}$ of 485 mg/kg with a 95% confidence interval of 324 to 677 mg/kg [23].

Compound 3 was tested in the psychomotor 6 Hz model at 32 mA and exhibited significant activity with an $ED_{50}$ of 80 mg/kg having a 95% confidence interval of 54.9-103.7.

In addition Compound 3 was evaluated quantitatively in the hippocampal kindling screen-rats model and exhibited high anticonvulsant activity with an $ED_{50}$ value of 35 mg/kg having a 95% confidence interval of 22.8-52.5.

Table 4 presents the experimental results of the tests conducted in the hippocampal Kindling screen-rats model, according to which the anticonvulsant profile of Compound 3 was evaluated.

TABLE 4

| Rat ID | Seizure Score | | After Discharge Duration (sec) | |
|---|---|---|---|---|
| | Before administration | After administration | Before administration | After administration |
| 1 | 5 | 0 | 93-103 | 4 |
| 2 | 5 | 0 | 28-75 | 14 |

As can be seen in Table 4, 15 minutes after intraperitoneal drug administration, Compound 3 demonstrated complete reduction of the seizure score from 5 to 0 and significantly decreased the after discharge duration.

The results also demonstrate that Compound 3 is a promising candidate as an effective mood stabilizer, based on its excellent ability to completely prevent seizures and significantly reduce "after discharge duration" in the hippocampal kindling test, which a widely accepted animal model for bipolar disorder [26].

Table 5 below presents the results obtained for Compound 3 in the Bicucullin and Picrotoxin assay in mice, showing the $ED_{50}$ values in mg/kg as measured in mice.

TABLE 5

| Assay | VPA $ED_{50}$ (mg/kg) [31] | Compound 3 $ED_{50}$ (mg/kg) |
|---|---|---|
| Bicucullin | 589 | 204.6 |
| Picrotoxin | 270 | 166.6 |

It should be noted that the bicucullin and picrotoxin tests were performed in mice and not in rats, therefore no comparison can be made between the MES and scMet $ED_{50}$'s evaluated in rats on the one hand and the bicucullin and picrotoxin $ED_{50}$'s determined in mice on the other hand.

The bicucullin and picrotoxin tests measure the ability of new drugs to provide complete protection against clonic threshold seizures induced by these two convulsant agents. The convulsant agents were administered only after the mice received the tested compounds, and the mice were observed for the presence or absence of a clonic seizure. Absence of clonic seizure is indicative of the ability of the tested compound to elevate the seizure threshold.

As can be seen in Table 5, Compound 3 exhibited significant protective activity against clonic threshold seizures, being 2.8 and 1.6 times more potent than valproic acid in the bicucullin and picrotoxin test respectively.

2-ethyl-3-methylvaleroylurea (Compound 4) was also found to exhibit promising anticonvulsant activity and low toxicity, having $ED_{50}$ in the MES assay in rats of 24 mg/kg, 14 mg/kg in the scMet assay in rats, and $TD_{50}$ of 97 mg/kg in rats. According to these results, Compound 4 exhibits a protective index (scMet) of 6.9 and a protective index (MES) of 4. This compound was first tested by Spielman et al. [19] and was reported to be inactive in the MES assay and only active at toxic doses in the scMet assay. The results presented herein clearly show the efficacy in the MES and scMet assay at non toxic levels.

Table 6 below summarizes the results of all assays conducted for some of the exemplary compounds according to the present embodiments.

TABLE 6

| | $ED_{50}$ (mg/kg) | | | | | $TD_{50}$ (mg/kg) in Rats |
|---|---|---|---|---|---|---|
| Compound | MES in Rats | scMet in Rats | 6 Hz, 44 mA in Mice | 6 Hz, 32 mA in Mice | Hippocampal kindling in Rats | |
| Compound 1 | 16 | 45.4 | 71 | 42.2 | 94> | 94.5 |
| Compound 1R | N/D | N/D | 56 | 43 | N/D | N/D |
| Compound 1S | N/D | N/D | 75 | 46 | N/D | N/D |
| Compound 2 | 32.7 | 15.7 | 48.6 | 43.3 | 200> | 55.6 |
| Compound 3 | 63.9 | 26 | N/D | 80 | 35.1 | 143 |
| Compound 4 | 24 | 14 | 48 | 21 | N/D | 97 |
| Compound 5 | N/D | N/D | N/D | N/D | N/D | N/D |
| Compound 6 | 53.8 | 76.8 | 105.4 | 57.8 | 180> | 232.2 |
| Compound 7 | >250 | 83 | N/D | N/D | N/D | <500 |
| Compound 8 | N/D | N/D | N/D | N/D | N/D | N/D |
| Compound 9 | 69.4 | 29.8 | N/D | N/D | N/D | 228.3 |

Neurotoxicity Assays:

The neurotoxicity of the compounds of the present embodiments was tested using rats which were treated by oral administration, and evaluated according to the "gait and stance" test, which assesses minimal neurotoxicity. The neurotoxicity assays were design to assess the effect of putative neurotoxicants on the normal activity of the nervous system, which can adversely disrupt or cause neuronal death, and damage other parts of the nervous system. The median neurological toxic dose ($TD_{50}$) was used for quantization of neurotoxicity. In some of the species the $TD_{50}$ was determined to be above a certain level, indicating a lower neurotoxicity than specified [23].

The protective index (PI), or margin of safety, is defined as the ratio of $TD_{50}$ and $ED_{50}$ ($PI=TD_{50}/ED_{50}$). The PI is used to show an effective differentiation between toxicity and activity, whereas the larger the PI value, the safer and more efficacious the antiepileptic drug is [23].

Results of Neurotoxicity Assays:

The protective index (PI) of exemplary acyl-urea derivative compounds, according to some embodiments of the invention, namely Compounds 1, 2 and 3, was compared to the protective index obtained for valproic acid, and the results are presented in Table 7 herein below.

TABLE 7

| Tested compound | PI in the MES test | PI in the scMet test |
|---|---|---|
| Valproic acid | 1.6 | 1.2 |
| Compound 1 | 6 | 2 |
| Compound 2 | 1.7 | 3.5 |
| Compound 3 | 2.2 | 5.5 |
| Compound 4 | 4 | 6.9 |

As can be seen in Table 7, a wide range of PI values was observed for the acyl-urea derivative compounds presented herein, all of which were higher than the PI observed for valproic acid. These results clearly demonstrate that a significant improvement in terms of pharmacological efficacy and safety is achieved with the acyl-urea derivative compounds presented herein as compared to valproic acid.

The $TD_{50}$ of Compounds 1 and 2 was 95 mg/kg and 56 mg/kg respectively following oral administration to rats. For comparison, the $TD_{50}$ of Reference Compound 1 was determined at 538 mg/kg following oral administration to rats [6], VPA exhibits a $TD_{50}$ value of 784 mg/kg [23], and Reference Compound 2 exhibits a $TD_{50}$ above 500 mg/kg [30].

The results for other exemplary compounds according to some embodiments are presented in Table 5 hereinabove.

Particular attention is drawn to compounds such as Compounds 4, 5, 6, 7 and 8, which were tested for anti-convulsant activity by Spielman and co-workers and were found to lack beneficial activity, but were found quite active by the present inventors, as presented hereinabove.

Altogether, the experimental results presented hereinabove clearly demonstrate that the acyl-urea derivative compounds presented herein and exemplified with Compounds 1, 2 and 3, have an unexpected potential as highly efficacious drugs for the treatment of epilepsy and other neurological and psychiatric diseases and disorders.

Results of Status Epilepricus (SE) Protection Assays:

As detailed hereinabove, the animal model used (i.e., pilocarpine) is characterized by a large number of spontaneous recurrent seizures as well as development of mossy-fiber sprouting. The model features both acute induced SE and chronic spontaneous seizures. An important feature of the model is the occurrence of spontaneous seizures post administration of the chemoconvulsant.

The tests were conducted using an exemplary compound according to some embodiments of the present invention, (a racemate of 2-ethyl-3-methyl-pentanoyl)-urea (VCU, Compound 4, valnoctyl urea), which is an urea amide of valnoctic acid having two chiral centers one in each of positions 2 and 3 (see, Table 1 hereinabove).

Table 8 presents the results of the basic anticonvulsant profile of VCU after i.p. administration to rats.

TABLE 8

| Dose (mg/kg) | Duration after first stage III seizure (hours) | Prot./Tested | Died | Average weight change (grams ± S.E.M.) | Comments |
|---|---|---|---|---|---|
| 18.75 | 0 | 3/7 | 0 | −7.9 ± 6.5 | |
| 37.5 | 0 | 6/8 | 0 | +8.8 ± 5.4 | Sedated |
| 75 | 0 | 8/8 | 0 | +15.6 ± 2.2 | Sedated |
| 37.5 | 0.25 | 9/15 | 0 | −13.3 ± 3.4 | |
| 75 | 0.25 | 8/8 | 0 | −3.1 ± 6.2 | Sedated |

As can be seen on Table 8, at time of pilocarpine administration (at a dose causing at least Stage III seizures, referred to herein as "Time 0") and immediately after administration of VCU, the number of protected animals per tested increased gradually with increasing dose until full protection was achieved at a dose of 75 mg/kg of VCU (see, Table 8 below). As can further be seen in Table 8, full protection was achieved even 15 minutes post VCU administration of 75 mg/kg.

Table 9 presents quantitative anticonvulsant data obtained in rats which were treated i.p. with VCU.

TABLE 9

| (ED50 Values) | | | | |
|---|---|---|---|---|
| TPE (hours) | Dose (mg/kg) | 95% C.I. | Slope | ±S.E.M. |
| 0 | 22.73 | 4.02-33.17 | 3.82 | 1.64 |

As can be seen in Table 9, the calculated $ED_{50}$ at time of peak effect (TPE), which equals time 0, is 22.73 mg/kg.

Tables 10 and 11 present the response data pertaining to the anticonvulsant profile of VCU 30 minutes after i.p. administration of various doses (75, 112.5 and 150 mg/kg) to rats, and thus provide information regarding VCU's protection against pilocarpine-induced seizures.

TABLE 10

| Dose (mg/kg) | Duration after first stage III seizure (hours) | Average weight change (grams ± S.E.M.) | Prot./tested | Died | Comment |
|---|---|---|---|---|---|
| 75 | 0.5 | −14.2 ± 1.3 | 4/8 | 2 | Sedated |
| 112.5 | 0.5 | −23.1 ± 3.2 | 6/8 | 0 | Sedated |
| 150 | 0.5 | −21.4 ± 2.4 | 6/8 | 1 | Sedated |

TABLE 11

| Dose (mg/kg) | Duration after first stage III seizure (hours) | Average weight change (grams ± S.E.M.) | Prot./tested | Died | Comment |
|---|---|---|---|---|---|
| 75 | 0.5 | −14.2 ± 1.3 | 4/8 | 2 | Sedated |
| 112.5 | 0.5 | −23.1 ± 3.2 | 6/8 | 0 | Sedated |
| 150 | 0.5 | −21.4 ± 2.4 | 6/8 | 1 | Sedated |

As can be seen in Tables 10 and 11, at doses above 112.5 mg/kg, 6/8 animals were protected 30 minutes post drug administration.

Tables 12 and 13 present the response data pertaining to the anticonvulsant profile of VCU after i.p. administration to rats, and provide additional information about the number of protected animals per tested animals at various VCU doses at time 0, 15 minutes and 30 hours after the administration of the tested compounds according to some embodiments of the present invention.

TABLE 12

| Dose (mg/kg) | Duration after first stage III seizure (hours) | Prot./Tested | Died | Average weight change (grams ± S.E.M.) |
|---|---|---|---|---|
| 100 | 0 | 8/8 | 0 | +9.4 ± 1.1 |
| 50 | 0 | 4/8 | 1 | −3.6 ± 6.5 |
| 100 | 0.25 | 1/8 | 0 | −17.5 ± 2.5 |

TABLE 13

| Dose (mg/kg) | Duration after first stage III seizure (hours) | Prot./Tested | Died | Average weight change (grams ± S.E.M.) |
|---|---|---|---|---|
| 200 | 30 | 2/6 | 1 | −18.0 ± 1.6 |

Table 14 presents the toxicity profile of VCU as determined after its i.p. administration to rats.

TABLE 14

| | Time (hours) | | | | |
|---|---|---|---|---|---|
| Dose (mg/kg) | 0.25 | 0.5 | 1 | 2 | 4 |
| 300 | 2/2 | 2/2 | 2/2 | 2/2 | 2/2 |
| 100 | 0/2 | 1/2 | 1/2 | 0/2 | 0/2 |

As can be concluded from the results presented hereinabove, Compound 4 displayed a remarkable capacity to halt the progression of SE, at a behaviorally toxic dose, when administered immediately after the first appearance of a Stage III seizure. Compound 4 was also very effective when administered 15 minutes after the first Stage III seizure ("Time 15"), Although less effective, it also decreased seizure activity 30 minutes after the first Stage III seizure, an effect which appears to be dose dependent.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited in the Text

1. Nau, H., *Valproic acid teratogenesis in mice after various administration and phenobarbital-pretreatment regimens: The parent drug and not one of the metabolites assayed is implicated as teratogen.* Fund. Appl. Toxicol., 1986. 6: p. 662-668
2. Baillie, T. A., *Metabolism of valproate to hepatotoxic intermediates.* Pharm Weekbl Sci, 1992. 14(3A): p. 122-5.
3. Baillie, T. A., Scheffels, P. R., ed. *Valproic acid, chemistry and biotransformation.* 4 ed. Antiepileptic Drugs, ed. R. H. M. R. H. Levy, B. S. Meldrum and E. Perucca. 1995, Raven Press: New York. 589-603.
4. Rettie, A. E., et al., *Cytochrome P-450-catalyzed formation of delta 4-VPA, a toxic metabolite of valproic acid.* Science, 1987. 235(4791): p. 890-3.
5. de Paulis, T., *ONO-2506. Ono.* Curr Opin Investig Drugs, 2003. 4(7): p. 863-7.
6. Sobol, E., M. Bialer, and B. Yagen, *Tetramethylcyclopropyl analogue of a leading antiepileptic drug, valproic acid. Synthesis and evaluation of anticonvulsant activity of its amide derivatives.* J Med Chem, 2004. 47(17): p. 4316-26.
7. Isoherranen, N., et al., *Anticonvulsant profile and teratogenicity of N-methyl-tetramethylcyclopropyl carboxamide: a new antiepileptic drug.* Epilepsia, 2002. 43(2): p. 115-26.
8. Isoherranen, N., B. Yagen, and M. Bialer, *New CNS-active drugs which are second-generation valproic acid: can they lead to the development of a magic bullet?* Curr Opin Neurol, 2003. 16(2): p. 203-11.
9. Isoherranen, N., et al., *Metabolism of a new antiepileptic drug, N-methyl-tetramethylcyclopropanecarboxamide, and anticonvulsant activity of its metabolites.* Epilepsy Res, 2004. 58(1): p. 1-12.
10. Winkler, I., et al., *Efficacy of antiepileptic tetramethylcyclopropyl analogues of valproic acid amides in a rat model of neuropathic pain.* Neuropharmacology, 2005. 49(8): p. 1110-20.
11. Winkler, I., et al., *Efficacy of antiepileptic isomers of valproic acid and valpromide in a rat model of neuropathic pain.* Br J Pharmacol, 2005. 146(2): p. 198-208.
12. Shimshoni, J., Dalton, E. C., Jenkins, A., Eyal, S., Ewen, K., Williams, R. S. B., Yagen, B., Harwood, J. A., Bialer, M., *Probing CNS-active analogues and amide derivatives of valproic acid for mood stabilizer properties.* Neuropsychopharmacology, TBP.
13. Shaltiel, G., et al., *Valproate decreases inositol biosynthesis.* Biol Psychiatry, 2004. 56(11): p. 868-74.
14. Swinyard, E. A. and J. E. Toman, *A comparison of the anticonvulsant actions of some phenylhydantoins and their corresponding phenylacetylureas.* J Pharmacol Exp Ther, 1950. 100(2): p. 151-7.
15. Moldenhauser, A., J. Chem. Soc., 1855. 102 (94).
16. Dilthey, F.a., J. Chem. Soc., 1904. 335: p. 366-7.
17. Newberry, J. Chem. Soc., 1925(125): p. 295
18. Stoughton, R. W., *Diacylureas. II. Preparation and properties of diacylureas derived from branched aliphatic acids.* J. Am. Chem. Soc., 1939. 61(2): p. 408-410.
19. Spielman, M. A., Geiszler, A. O., Close, W. J., *Anticonvulsant Drugs. II. Some acetylureas.* J. Am. Chem. Soc., 1948. 70: p. 4189-4191.
20. Mrongovius, R. I., *Structure-activity correlations for central depressant Acylureas and alkylureas.* Eur. J. Med. Chem., 1975. 10: p. 474-479.
21. Tantisira, B., et al., *Preliminary evaluation of the anticonvulsant activity of a valproic acid analog: N-(2-propylpentanoyl)urea.* Res Commun Mol Pathol Pharmacol, 1997. 97(2): p. 151-64.
22. Goldstein, L. and C. C. Pfeiffer, *Quantitative EEG analysis of single-dose effect relationships in normal volunteers of Pacinox (capuride), a new antianxiety drug.* Biol Psychiatry, 1971. 3(2): p. 165-72.
23. White, H. S., ed. *General principles. Discovery and preclinical development of antiepileptic drugs.* 5 ed. Antiepileptic drugs, ed. M. R. Levy R H, Meldrum B S, Perucca E. 2002, Lippincott-Raven: Philadelphia. 36-48.
24. Furniss, B. S. H., A. J.; Smith, P. W. G.; Tatchell, A. R., *Vogel's Textbook of Practical Organic Chemistry*, in New York. 1989, Prentice Hall. p. 720-723.

25. Spiegelstein, O., et al., *Enantioselective synthesis and teratogenicity of propylisopropyl acetamide, a CNS-active chiral amide analogue of valproic acid*. Chirality, 1999. 11(8): p. 645-50.
26. Weiss, S. R. and R. M. Post, *Kindling: separate vs. shared mechanisms in affective disorders and epilepsy*. Neuropsychobiology, 1998. 38(3): p. 167-80.
27. Lothman, E. W., et al., *Screening and characterization of antiepileptic drugs with rapidly recurring hippocampal seizures in rats*. Epilepsy Res, 1988. 2(6): p. 367-79.
28. Cavalheiro, E. A., *The pilocarpine model of epilepsy*. The Italian Journal of Neurological Sciences, 1995. 16(1-2): p. 33-37.
29. Racine, R. J., *Modification of seizure activity by electrical stimulation. II. Motor seizure*. Electroencephalogr Clin Neurophysiol, 1972. 32(3): p. 281-94.
30. Bialer, M., et al., *Pharmacokinetic analysis and antiepileptic activity of tetra-methylcyclopropane analogues of valpromide*. Pharm Res, 1996. 13(2): p. 284-9.
31. White, H. S., Woodhead, J. H., Wilcox, K. S., Stables, J. P., Kupferberg, H. J.; Wolf, H. H., *Discovery and Preclinical Development of Antiepileptic Drugs*, in *Antiepileptic Drugs*, R. H. Levy, Mattson, R. H., Meldrum, B. S., Perucca, E., Editor. 2002, Lippincott Williams & Wilkins: New York. p. 36-48.

What is claimed is:

1. A method of treating a seizure of epilepsy, the method comprising administering to a subject in need thereof a therapeutically effective amount of a compound 1-(3,3-dimethylbutyryl)urea (compound 3, TBU), having the formula:

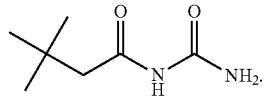

2. The method of claim 1, wherein said seizure of epilepsy is selected from the group consisting of complex partial seizures, chemically-induced seizure, status epilepticus and febrile seizure.

* * * * *